United States Patent
Seo et al.

(10) Patent No.: US 10,982,236 B2
(45) Date of Patent: Apr. 20, 2021

(54) RECOMBINANT YEAST FOR PRODUCING 2,3-BUTANEDIOL INCLUDING PYRUVATE DECARBOXYLASE DERIVED FROM CANDIDA TROPICOLIS AND METHOD FOR PRODUCING 2,3-BUTANEDIOL USING THE SAME

(71) Applicant: SEOUL NATIONAL UNIVERSITY R&DB FOUNDATION, Seoul (KR)

(72) Inventors: Jin Ho Seo, Seoul (KR); Jin Woo Kim, Gunpo-si (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 0 days.

(21) Appl. No.: 16/337,765

(22) PCT Filed: May 15, 2017

(86) PCT No.: PCT/KR2017/005008
§ 371 (c)(1),
(2) Date: Mar. 28, 2019

(87) PCT Pub. No.: WO2018/212366
PCT Pub. Date: Nov. 22, 2018

(65) Prior Publication Data
US 2019/0292570 A1    Sep. 26, 2019

(51) Int. Cl.
| | | |
|---|---|---|
| *C12P 7/16* | (2006.01) | |
| *C12P 7/18* | (2006.01) | |
| *C12N 1/16* | (2006.01) | |
| *C12N 1/19* | (2006.01) | |
| *C12N 9/88* | (2006.01) | |
| *C12N 9/02* | (2006.01) | |
| *C12N 9/04* | (2006.01) | |
| *C12N 1/14* | (2006.01) | |
| *C12N 9/10* | (2006.01) | |
| *C12R 1/865* | (2006.01) | |
| *C12N 15/81* | (2006.01) | |

(52) U.S. Cl.
CPC .................. *C12P 7/18* (2013.01); *C12N 1/14* (2013.01); *C12N 9/1022* (2013.01); *C12N 15/81* (2013.01); *C12P 7/16* (2013.01); *C12R 1/865* (2013.01); *C12Y 202/01006* (2013.01)

(58) Field of Classification Search
None
See application file for complete search history.

(56) References Cited

FOREIGN PATENT DOCUMENTS

| KR | 10-2015-0068581 A | 6/2015 |
|---|---|---|
| KR | 10-1590993 B1 | 2/2016 |
| KR | 10-2016-0093492 A | 8/2016 |
| KR | 10-2017-0028055 A | 3/2017 |
| WO | 2011/041426 A1 | 4/2011 |
| WO | 2016/012557 A1 | 1/2016 |

OTHER PUBLICATIONS

Kim et al., "Enhanced production of 2,3-butanediol by engineered *Saccharomyces cerevisiae* through fine-tuning of pyruvate decarboxylase and NADH oxidase activities", Biotechnol. Biofuels 9:265, 2016, 12 pages (Year: 2016).*
Zhou et al., Cell Mol Life Sci 63:2260-2290, 2006 (Year: 2006).*
Kozak, Gene 234:187-208, 1999 (Year: 1999).*
Choi, E., "Production of 2,3-butanediol from glucose and galactose in engineered *Saccharomyces cerevisiae*", Thesis, Seoul National University, Feb. 2016 (Year: 2016).*
Sakuragi et al., Biosci. Biotechnol. Biochem. 79:314-320, 2015 (Year: 2015).*
Kim et al., Biores. Technol. 191:512-519, 2015 (Year: 2015).*
Knudsen et al., "Exploring the potential of the glycerol-3-phosphate dehydrogenase 2 (GPD2) promoter for recombinant gene expression in *Saccharomyces cerevisiae*", Biotechnol. Reports 7:107-119, 2015 (Year: 2015).*
Gunawan et al., "Yeast pyruvate decarboxylases: variation in biocatalytic characteristics for (R)-phenylacetylcarbinol production", FEMS Yeast Res, 2007, vol. 7, pp. 33-39.
Kim et al., "Deletion of glycerol-3-phosphate dehydrogenase genes improved 2,3-butanediol production by reducing glycerol production in pyruvate decarboxylase-deficient *Saccharomyces cerevisiae*", Journal of Biotechnology, 2019, vol. 304, pp. 31-37.
Kim et al., "Metabolic engineering of *Saccharomyces cerevisiae* for 2,3-butanediol production", Appl Microbial Biotechnol, (2017), vol. 101, pp. 2241-2250.
Kim et al., "Efficient production of 2, 3-butanediol in *Saccharomyces cerevisiae* by eliminating ethanol and glycerol production and redox rebalancing", Metabolic Engineering, (2015), vol. 31, pp. 94-101.
Ng et al., "Production of 2,3-butanediol in *Saccharomyces cerevisiae* by in silico aided metabolic engineering", Microbial Cell Factories, (2012), vol. 11, p. 68 (1-14).

* cited by examiner

*Primary Examiner* — David Steadman
(74) *Attorney, Agent, or Firm* — Vorys, Sater, Seymour and Pease LLP; Mih Suhn Koh

(57) ABSTRACT

Provided is a recombinant *Saccharomyces cerevisiae* for producing 2,3-butanediol, wherein all GPD1 and GPD2 genes involved in glycerol biosynthesis are removed and a gene encoding NADH oxidase is introduced, and wherein pyruvate decarboxylase activity is inactivated and *Candida tropicalis* PDC1 gene encoding *Candida tropicalis* pyruvate decarboxylase 1-is introduced, and wherein expression of the *Candida tropicalis* PDC1 gene is regulated by a GPD2 promoter.

9 Claims, 19 Drawing Sheets
Specification includes a Sequence Listing.

FIG. 14

ATGTCTGCTGCTGATAGATTAAACTTCCGGCCACTGAATGCTGGTAGAAAGAG
AAGTTCCTCTTCTGTTTCTTTGAAGGCTGCCGAAAAGCCTTTCAAGTAAACTGTGATTGGAT
CTGGTAACTGGGGTACTACTATTGCCAAGGTGGTTGCGAAAAATTGTAAGGGATACCAGAA
GTTTTCGCTCCAATAGTACAAATGTGGGTGTTCGAAGAAGAGATCAATGTGAAAAATTGAC
TGAAATCATAAATACTAGACATCAAAACGTGAAATACTTGCCTGGCATCACTCACCGACAA
TTTGGTTGCTAATCCAGACTTGATTCAGTCAAGGATGCGACATCATCGTTTTCAACAT
TCCACATCAATTTTTGCCCGTATCTGTAGCCAATGAAAGGTCATGTTGATTCACACGTCAG
AGCTATCTCCTGTCTAAAGGGTTTTGAAGTTGGGTGCTAAAGGTGTCCAATTGCTATCTCTTA
CATCACTGAGGAACTAGGTATTCAATGTGGTGCTCTATCTGGTGCTAACATTGCCACCGAAGT
CGCTCAAGAACACTGGTCTGAAACAGGATAAGGTTCTAAAGGCCTTGTTCCACAGACCTTACTTCCACGT
GAGGGCAAGGACGTCGAACATGTTGCTGGTATCTCCATCTGTGGTGCTTTGAAGAACGTTGTTGCCTT
TAGTGTCATCGAAGATGTGCTGGTATCTCCATCTGTGGTGCTTTGAAGAACGTTGTTGCCTT
AGGTTGGTTTCGTCGAAGGTCATCAGATTCGGTGGTAACAACGCTTCTGCTGCCATCCAAAGA
GTCGGTTTGGGTGAGATCATCATCGAGATTCGGTCAAATGTTTTCCCAGAATCTAGAAGAAAAC
ATACTACCAAGAGTCTGCTGGTGTTGCTGATTTGATCACCACCTGCGCTGGTGGTAGAAACG
TCAAGGTTGCTAGGCTAAGGCTACTTCTGGTAAGGACGCCTGGGAATGTGAAAAGGAGTT
GTTGAATGGCCAATCCGCTCAAGGTTTAATTACCTGCAAAGAAGTTCACGAATGGTTGGAA
ACATGTGGCTCTGTCGAAGACTTCCCATTATTGAAGCCGTATACCAAATGTTTACAACAAC
TACCCAATGAAGAACCTGCCGGAGACATGATTGAAGAATTAGATCTACATGAAGATTAG

SEQ ID NO: 14

FIG. 15

ATGCTTGCTGTCAGAAGATTAACAAGATACACATTCTAAGGGAAGGAATCGGGTGTTATAT
ACTGGTGGTGCATATAAAATTTGCCTTCAAGATCTACTTTCCTAAGAAGATCATTATTACAA
ACACAACTGCACTCAAAGATGACTGCTATATACTAATATCAAACAGACAAAACACTGTCATGA
GTAACATCCTATCAGAAGATGGGACTGGCGTGTCAATTGTACATTGAAACGTGCGCCCTT
CAAGGTTACAGTGATGGTTCTGGTAACTGGGGACCACCATCGCCAAAGTCATTGCCGGAA
AACACAGAATTGCATTCCCATATCTCGAGCCAGAGGTGAGAATGTGGGTTTTGATGAAAA
GATGGGGACGAAAAATCTGACGGATATCATAAATACAAGAACACCAGAACGTAAATATCTAC
CCAATATTGACCTGCCCATAATCTAGTGGCGATCTGATCTTTACACTCCATCAAGGGTGC
TGACATCCTTGTTTTCAACATCCCCTCATCAATTTTTACCAAACATAGTCAAACAATTGCAAGG
CCAGTGGCCCTCATGTAAGGGCCATCTGTGTCTAAAAGGGTTGGAGTTGGGCTCAAGG
GTGTGCAATTGCTATCCTCCTAGTTACTGATGAGTTAGGAATCCAATGTGGCCACTATCTG
GTGCAAACTTGGCACCGGAAGTGGCCAAGGAGCATTGGTCGGAAACCACCGTGGCTACCA
ACTACCAAAAGGATTATCAAGGTGATGGCCAAGGAGTAGATCATAAGATTTGAAATTGCTGT
TCCAACAGACCTTACTTCCAGTGCACTGCATGTCATGATGATGTTGCTGTGTATATCCATTGCCGGGTGC
CTTGAAGAACGTGCTGGCACTGCACTGCACTGGTTCGTAGAAGGTATGGGATGGGGTAACAAT
GCCTCCGCAGCCATTCAAAGGCTGGGTTAGGTGAAATTATCAAGTTCGGTAGAAATGTTTT
CCAGAAATCAAAGTGCAGAACCTACTATCAAGAAATCCGCTGGTGTTGCAGAATCTGATCACCA
CCTGCTCAGGCGGGTAGAAAACGTCAAGTTGCCACATACATGGCCAAGACCGGTAAGTCAGC
CTTGGAAGCAGAAAAGGAATTGCTAAGGTCAATCCGCCCAAGGGATAATCACATGCAGA
GAAGTTCACGAGTGGCTACAAACATGTGAGTGACCTGAAGAATTCCCATTATCGAGGCAGT
CTACCAGATAGTCTACAACAACGTCCGCATGGAAGAACCTACCGGGAGATGATTGAAGAGCTA
GACATCGATGACGAATAG

SEQ ID NO: 15

SEQUENCE LISTING

<160> NUMBER OF SEQ ID NOS: 19

<210> SEQ ID NO 1
<211> LENGTH: 1704
<212> TYPE: DNA
<213> ORGANISM: Candida tropicalis

<400> SEQUENCE: 1

```
atgtctgaaa ttactttggg tagattcttc tttgaaagat gcaccaatt gcaagttgac      60
accgttttcg gttaccagg tgattttaac ttggctttat tagataaaat ctacgaagtc     120
gatggtatga gatgggctgg taacgccaat gaattgaacg ctggttacgc tgctgatggt    180
tacgccagag ttaatccaaa tggtttggct gctttagtct ccaccttcgg tgttggtgaa    240
ttgtctttga ctaacgccat tgctggttct tactctgaac acgttggtat cattaacttg    300
gttggtgttc catcttcttc tgctcaagct aaacaattgt tgttgcacca caccttgggt    360
aacggtgatt tcactgtttt ccacagaatg ttcaagaaca tttctcaaac ttctgctttc    420
atctccgacc aaacactgc tgcttctgaa attgacagat gtatcagaga tgcttacgtt    480
taccaaagac cagtttacat tggtttgcca tctaacttgg ttgatgttaa agttccaaaa    540
tctttgttgg acaaaaaaat tgacttgtcc ttgcatccaa atgaaccaga tcccaagct    600
gaagttgttg aaaccgttga aaattcatt tctgaagctt ctaacccagt tatcttggtt    660
gatgcttgtg ctatcagaca caactgtctt aaagaagttg ctgaattgat tgctgaaact    720
caattcccag tcttccaccac tccaatgggt aaatcaagtg ttgatgaatc caacccaaga    780
ttcggtggtg tttacgttgg ttctttgtct tctccagatg ttaagaagc cgttgaaagt    840
gctgacttgg tcttatctgt tggtgctatg ttgtctgatt caacactgg tgcttttctct    900
tacaactaca agaccagaaa tgttgttgaa ttccactctg attacaccaa gatcagacaa    960
gctactttcc caggtgtcca atgaaagaa gctttgcaag ttttgttgaa gactgtcaag   1020
aaatctgtca atccaaaata cgtcccagct ccagttccag ctaccaaagc tattaccact   1080
ccaggtaaca cgacccagt ctctcaagaa tacttgtgga aaagtttc tgactggttc   1140
caagaaggtg atgttatcat ttctgaaacc ggtacctctg ctttcggtat tgtccaatct   1200
aaattcccaa agaatgccat tggtatttcc caagtcttgt ggggttctat tggttacgct   1260
actggtgcta cttgtggtgc tgctatggct gctcaagaaa ttgacccaaa gaagagagtt   1320
atcttgttca ctggtgatgg ttcttttgcaa ttgactgtcc aagaaatctc taccatgtgt   1380
aaatgggatt gttacaacac ctatctttac gttttgaaca acgatggtta caccattgaa   1440
agattgattc acggtgaaaa agctcaatat aacgacattc aaccatggaa caacttgcaa   1500
cttttgccat tgttcaacgc taagaaatac gaaaccaaga gaatttctac tgttggtgaa   1560
ttgaacgatt tgttcactaa caagaatttt gctgttccag acagaattag aatggttgaa   1620
attatgttgc cagttatgga tgctccagct aacttggttg cccaagctaa caatctgct   1680
gctaccaacg ctgctcaaga taa                                           1704
```

<210> SEQ ID NO 2
<211> LENGTH: 567
<212> TYPE: PRT
<213> ORGANISM: Candida tropicalis

<400> SEQUENCE: 2

```
Met Ser Glu Ile Thr Leu Gly Arg Phe Phe Phe Glu Arg Leu His Gln
 1               5                  10                  15
```

```
Leu Gln Val Asp Thr Val Phe Gly Leu Pro Gly Asp Phe Asn Leu Ala
             20                  25                  30

Leu Leu Asp Lys Ile Tyr Glu Val Asp Gly Met Arg Trp Ala Gly Asn
         35                  40                  45

Ala Asn Glu Leu Asn Ala Gly Tyr Ala Ala Asp Gly Tyr Ala Arg Val
    50                  55                  60

Asn Pro Asn Gly Leu Ala Ala Leu Val Ser Thr Phe Gly Val Gly Glu
65                  70                  75                  80

Leu Ser Leu Thr Asn Ala Ile Ala Gly Ser Tyr Ser Glu His Val Gly
                85                  90                  95

Ile Ile Asn Leu Val Gly Val Pro Ser Ser Ala Gln Ala Lys Gln
             100                 105                 110

Leu Leu Leu His His Thr Leu Gly Asn Gly Asp Phe Thr Val Phe His
         115                 120                 125

Arg Met Phe Lys Asn Ile Ser Gln Thr Ser Ala Phe Ile Ser Asp Pro
    130                 135                 140

Asn Thr Ala Ala Ser Glu Ile Asp Arg Cys Ile Arg Asp Ala Tyr Val
145                 150                 155                 160

Tyr Gln Arg Pro Val Tyr Ile Gly Leu Pro Ser Asn Leu Val Asp Val
                165                 170                 175

Lys Val Pro Lys Ser Leu Leu Asp Lys Lys Ile Asp Leu Ser Leu His
             180                 185                 190

Pro Asn Glu Pro Glu Ser Gln Ala Glu Val Val Glu Thr Val Glu Lys
         195                 200                 205

Phe Ile Ser Glu Ala Ser Asn Pro Val Ile Leu Val Asp Ala Cys Ala
    210                 215                 220

Ile Arg His Asn Cys Leu Lys Glu Val Ala Glu Leu Ile Ala Glu Thr
225                 230                 235                 240

Gln Phe Pro Val Phe Thr Thr Pro Met Gly Lys Ser Ser Val Asp Glu
                245                 250                 255

Ser Asn Pro Arg Phe Gly Gly Val Tyr Val Gly Ser Leu Ser Ser Pro
             260                 265                 270

Asp Val Lys Glu Ala Val Glu Ser Ala Asp Leu Val Leu Ser Val Gly
         275                 280                 285

Ala Met Leu Ser Asp Phe Asn Thr Gly Ala Phe Ser Tyr Asn Tyr Lys
    290                 295                 300

Thr Arg Asn Val Val Glu Phe His Ser Asp Tyr Thr Lys Ile Arg Gln
305                 310                 315                 320

Ala Thr Phe Pro Gly Val Gln Met Lys Glu Ala Leu Gln Val Leu Leu
                325                 330                 335

Lys Thr Val Lys Lys Ser Val Asn Pro Lys Tyr Val Pro Ala Pro Val
             340                 345                 350

Pro Ala Thr Lys Ala Ile Thr Thr Pro Gly Asn Asn Asp Pro Val Ser
         355                 360                 365

Gln Glu Tyr Leu Trp Arg Lys Val Ser Asp Phe Gln Glu Gly Asp
    370                 375                 380

Val Ile Ile Ser Glu Thr Gly Thr Ser Ala Phe Gly Ile Val Gln Ser
385                 390                 395                 400

Lys Phe Pro Lys Asn Ala Ile Gly Ile Ser Gln Val Leu Trp Gly Ser
                405                 410                 415

Ile Gly Tyr Ala Thr Gly Ala Thr Cys Gly Ala Ala Met Ala Ala Gln
             420                 425                 430

Glu Ile Asp Pro Lys Lys Arg Val Ile Leu Phe Thr Gly Asp Gly Ser
```

```
        435            440            445
Leu Gln Leu Thr Val Gln Glu Ile Ser Thr Met Cys Lys Trp Asp Cys
    450                455                460

Tyr Asn Thr Tyr Leu Tyr Val Leu Asn Asn Asp Gly Tyr Thr Ile Glu
465                470                475                480

Arg Leu Ile His Gly Glu Lys Ala Gln Tyr Asn Asp Ile Gln Pro Trp
                485                490                495

Asn Asn Leu Gln Leu Leu Pro Leu Phe Asn Ala Lys Lys Tyr Glu Thr
            500                505                510

Lys Arg Ile Ser Thr Val Gly Glu Leu Asn Asp Leu Phe Thr Asn Lys
        515                520                525

Glu Phe Ala Val Pro Asp Arg Ile Arg Met Val Glu Ile Met Leu Pro
    530                535                540

Val Met Asp Ala Pro Ala Asn Leu Val Ala Gln Ala Lys Gln Ser Ala
545                550                555                560

Ala Thr Asn Ala Ala Gln Glu
            565
```

<210> SEQ ID NO 3
<211> LENGTH: 1144
<212> TYPE: DNA
<213> ORGANISM: Saccharomyces cerevisiae

<400> SEQUENCE: 3

```
caaaaacgac atatctatta tagtggggag agtttcgtgc aaataacaga cgcagcagca    60
agtaactgtg acgatatcaa ctcttttttt attatgtaat aagcaaacaa gcacgaatgg   120
ggaaagccta tgtgcaatca ccaaggtcgt ccctttttc ccatttgcta atttagaatt    180
taagaaaacc aaaagaatga agaaagaaaa caaatactag ccctaaccct gacttcgttt   240
ctatgataat accctgcttt aatgaacggt atgccctagg gtatatctca ctctgtacgt   300
tacaaactcc ggttatttta tcggaacatc cgagcacccg cgccttcctc aacccaggca   360
ccgcccccag gtaaccgtgc gcgatgagct aatcctgagc catcacccac cccacccgtt   420
gatgacagca attcgggagg gcgaaaaata aaaactggag caaggaatta ccatcaccgt   480
caccatcacc atcatatcgc cttagcctct agccatagcc atcatgcaag cgtgtatctt   540
ctaagattca gtcatcatca ttaccgagtt tgttttcctt cacatgatga agaaggtttg   600
agtatgctcg aaacaataag acgacgatgg ctctgccatt gttatattac gcttttgcgg   660
cgaggtgccg atgggttgct gaggggaaga gtgtttagct tacggaccta ttgccattgt   720
tattccgatt aatctattgt tcagcagctc ttctctaccc tgtcattcta gtatttttt   780
ttttttttt tggttttact ttttttttctt cttgcctttt tttcttgtta cttttttct     840
agtttttttt ccttccacta agcttttcc ttgatttatc cttgggttct tcttctact    900
cctttagatt ttttttttat atattaattt ttaagtttat gtattttggt agattcaatt   960
ctctttcct ttccttttcc ttcgctcccc ttccttatca atgcttgctg tcagaagatt   1020
aacaagatac acattcctta agcgaacgca tccggtgtta tatactcgtc gtgcatataa   1080
aattttgcct tcaagatcta ctttcctaag aagatcatta ttacaaacac aactgcactc   1140
aaag                                                                  1144
```

<210> SEQ ID NO 4
<211> LENGTH: 1341
<212> TYPE: DNA
<213> ORGANISM: Lactococcus lactis subsp. cremoris MG1363

<400> SEQUENCE: 4

```
atgaaaatcg tagttatcgg tacaaaccac gcaggcattg ctacagcgaa tacattactt      60
gaacaatatc ccgggcatga aattgtcatg attgaccgta atagcaacat gagttatcta     120
ggttgtggca cagcaatttg ggttggaaga caaattgaaa aaccagatga attattttat     180
gccaaagcag aggattttga ggcaaaaggg gtaaaatttt tgactgaaac agaagtttca     240
gaaattgatt ttgctaataa gaaagtttat gcaaaaacta aatctgatga tgaaataatt     300
gaagcttacg acaagcttgt tttagcaaca ggttcacgtc caattattcc taatctacca     360
ggcaaagacc ttaagggaat tcattttctg aaacttttc aagaaggtca agcaattgac      420
gcagaatttg ccaaagaaaa agtcaagcgt atcgcagtca ttggtgcagg atatatcggt     480
acagagattg cggaagcagc taaacgtcgg ggtaaagaag ttcttctctt tgacgctgaa     540
aatacttcac ttgcatcata ttatgatgaa gaatttgcca aaggaatgga tgaaaacctt     600
gctcaacatg gaattgaact tcattttgga gaactggcca agaatttaa agcgaatgag      660
gaaggttatg tatcacaaat cgtaaccaac aaggcgactt atgatgttga tcttgtcatc     720
aattgtattg gttttactgc caacagtgcc ttggcaagtg ataagttagc taccttcaaa     780
aatggcgcaa tcaaggtgga taagcatcaa caaagtagtg atccagatgt ttacgcggta     840
ggtgatgttg cgacaattta ttctaatgcc ttgcaagatt ttacttatat cgctcttgcc     900
tcaaacgctg ttcggtcagg aattgtcgca ggacacaata ttggtggaaa agaattagaa     960
tctgttggtg ttcaaggttc taatggtatt tcgattttg gttacaatat gacttctaca    1020
ggactttctg ttaaagctgc taaaaaatta ggtttagaag tttcatttag tgattttgaa    1080
gataaacaaa aagcttggtt tcttcatgaa acaacgata gtgtgaaaat tcgtatcgta     1140
tatgagacaa aagtcgcag aattattgga gcacaacttg ctagtaaaag tgagataatt     1200
gcaggaaata taaatatgtt cagtttagcg attcaagaga aaaaaacaat tgatgaacta    1260
gctttgcttg atttattctt tctccccac ttcaacagtc catataatta tatgacagtt      1320
gcagctttga atgccaaata a                                               1341
```

<210> SEQ ID NO 5
<211> LENGTH: 289
<212> TYPE: DNA
<213> ORGANISM: Saccharomyces cerevisiae

<400> SEQUENCE: 5

```
atttggcgag cgttggttgg tggatcaagc ccacgcgtag gcaatcctcg agcagatccg      60
ccaggcgtgt atatatagcg tggatggcca ggcaacttta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289
```

<210> SEQ ID NO 6
<211> LENGTH: 655
<212> TYPE: DNA
<213> ORGANISM: Saccharomyces cerevisiae

<400> SEQUENCE: 6

```
agtttatcat tatcaatact cgccatttca aagaatacgt aaataattaa tagtagtgat       60
tttcctaact ttatttagtc aaaaaattag ccttttaatt ctgctgtaac ccgtacatgc     120
```

-continued

```
ccaaaatagg gggcgggtta cacagaatat ataacatcgt aggtgtctgg gtgaacagtt      180
tattcctggc atccactaaa tataatggag cccgcttttt aagctggcat ccagaaaaaa      240
aaagaatccc agcaccaaaa tattgttttc ttcaccaacc atcagttcat aggtccattc      300
tcttagcgca actacagaga acaggggcac aaacaggcaa aaacgggca caacctcaat       360 ggagtgatgc aacctgcctg agtaaatga tgacacaagg caattgaccc acgcatgtat       420
ctatctcatt tcttacacc ttctattacc ttctgctctc tctgatttgg aaaaagctga      480 aaaaaaggt tgaaaccagt tccctgaaat tattcccta cttgactaat aagtatataa       540
agacggtagg tattgattgt aattctgtaa atctatttct taaacttctt aaattctact     600
tttatagtta gtcttttttt tagttttaaa acaccagaac ttagtttcga cggat         655
```

```
<210> SEQ ID NO 7
<211> LENGTH: 22
<212> TYPE: DNA
<213> ORGANISM: Artificial Sequence
<220> FEATURE:
<223> OTHER INFORMATION: F_CYC1P

<400> SEQUENCE: 7
cgagctcatt tggcgagcgt tg                                              22

<210> SEQ ID NO 8
<211> LENGTH: 32
<212> TYPE: DNA
<213> ORGANISM: Artificial Sequence
<220> FEATURE:
<223> OTHER INFORMATION: R_CYC1P

<400> SEQUENCE: 8
cgcggatcct tagtgtgtgt atttgtgttt gc                                   32

<210> SEQ ID NO 9
<211> LENGTH: 32
<212> TYPE: DNA
<213> ORGANISM: Artificial Sequence
<220> FEATURE:
<223> OTHER INFORMATION: F_GPD2P

<400> SEQUENCE: 9
cgagctccaa aaacgacata tctattatag tg                                   32

<210> SEQ ID NO 10
<211> LENGTH: 29
<212> TYPE: DNA
<213> ORGANISM: Artificial Sequence
<220> FEATURE:
<223> OTHER INFORMATION: R_GPD2P

<400> SEQUENCE: 10
cgcggatccc tttgagtgca gttgtgttt                                       29

<210> SEQ ID NO 11
<211> LENGTH: 34
<212> TYPE: DNA
<213> ORGANISM: Artificial Sequence
<220> FEATURE:
<223> OTHER INFORMATION: F_nox

<400> SEQUENCE: 11
cgcggatcca aaatgaaaat cgtagttatc ggta                                 34
```

```
<210> SEQ ID NO 12
<211> LENGTH: 29
<212> TYPE: DNA
<213> ORGANISM: Artificial Sequence
<220> FEATURE:
<223> OTHER INFORMATION: R_XhoI_nox

<400> SEQUENCE: 12
ccgctcgagt ttatttggca ttcaaagct                                29

<210> SEQ ID NO 13
<211> LENGTH: 30
<212> TYPE: DNA
<213> ORGANISM: Artificial Sequence
<220> FEATURE:
<223> OTHER INFORMATION: R_SalI_nox

<400> SEQUENCE: 13
acgcgtcgac tttatttggc attcaaagct                               30

<210> SEQ ID NO 14
<211> LENGTH: 1176
<212> TYPE: DNA
<213> ORGANISM: Artificial Sequence
<220> FEATURE:
<223> OTHER INFORMATION: GPD1
<220> FEATURE:
<221> NAME/KEY: misc_feature
<222> LOCATION: (109)..(111)
<223> OTHER INFORMATION: these nucleotides are mutated

<400> SEQUENCE: 14
atgtctgctg ctgctgatag attaaactta acttccggcc acttgaatgc tggtagaaag     60
agaagttcct cttctgtttc tttgaaggct gccgaaaagc ctttcaagta aactgtgatt    120
ggatctggta actggggtac tactattgcc aaggtggttg ccgaaaattg taagggatac    180
ccagaagttt tcgctccaat agtacaaatg tgggtgttcg aagaagagat caatggtgaa    240
aaattgactg aaatcataaa tactagacat caaaacgtga atacttgcc tggcatcact     300 ctacccgaca atttggttgc taatccagac ttgattgatt cagtcaagga tgtcgacatc    360
atcgttttca acattccaca tcaattttg ccccgtatct gtagccaatt gaaaggtcat     420
gttgattcac acgtcagagc tatctcctgt ctaaagggtt tgaagttgg tgctaaaggt     480 gtccaattgc tatcctctta catcactgag gaactagta ttcaatgtgg tgctctatct     540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atggccaatc cgctcaaggt   1020
ttaattacct gcaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                             1176

<210> SEQ ID NO 15
```

```
<211> LENGTH: 1324
<212> TYPE: DNA
<213> ORGANISM: Artificial Sequence
<220> FEATURE:
<223> OTHER INFORMATION: GPD2
<220> FEATURE:
<221> NAME/KEY: misc_feature
<222> LOCATION: (190)..(192)
<223> OTHER INFORMATION: these nucleotides are mutated

<400> SEQUENCE: 15
atgcttgctg tcagaagatt aacaagatac acattcctta agcgaacgca tccggtgtta      60
tatactcgtc gtgcatataa aattttgcct tcaagatcta ctttcctaag aagatcatta     120
ttacaaacac aactgcactc aaagatgact gctcatacta atatcaaaca gcacaaacac     180
tgtcatgagt aacatcctat cagaagatcg gactctgccg tgtcaattgt acatttgaaa     240
cgtgcgccct tcaaggttac agtgattggt tctggtaact gggggaccac catcgccaaa     300
gtcattgcgg aaaacacaga attgcattcc catatcttcg agccagaggt gagaatgtgg     360
gtttttgatg aaaagatcgg cgacgaaaat ctgacggata tcataaatac aagacaccag     420
aacgttaaat atctacccaa tattgacctg ccccataatc tagtggccga tcctgatctt     480
ttacactcca tcaagggtgc tgacatcctt gttttcaaca tccctcatca attttttacca    540
aacatagtca acaattgca aggccacgtg gcccctcatg taagggccat ctcgtgtcta      600
aaagggttcg agttgggctc caagggtgtg caattgctat cctcctatgt tactgatgag     660
ttaggaatcc aatgtggcgg cactatctgg tgcaaacttg gcaccggaag tggccaagga     720
gcattggtcc gaaaccaccg tggcttacca actaccaaag gattatcaag gtgatggcaa     780
ggatgtagat cataagattt tgaaattgct gttccacaga ccttacttcc acgtcaatgt     840
catcgatgat gttgctggta tatccattgc cggtgccttg aagaacgtcg tggcacttgc     900
atgtggtttc gtagaaggta tgggatgggg taacaatgcc tccgcagcca ttcaaaggct     960
gggtttaggt gaaattatca agttcggtag aatgttttttc ccagaatcca agtcgagac   1020
ctactatcaa gaatccgctg tgttgcaga tctgatcacc acctgctcag gcggtagaaa    1080
cgtcaaggtt gccacataca tggccaagac cggtaagtca gccttggaag cagaaaagga    1140
attgcttaac ggtcaatccg cccaagggat aatcacatgc agagaagttc acgagtggct    1200
acaaacatgt gagttgaccc aagaattccc attattcgag gcagtctacc agatagtcta    1260
caacaacgtc cgcatggaag acctaccgga gatgattgaa gagctagaca tcgatgacga    1320
atag                                                                1324

<210> SEQ ID NO 16
<211> LENGTH: 67
<212> TYPE: DNA
<213> ORGANISM: Artificial Sequence
<220> FEATURE:
<223> OTHER INFORMATION: Nucleotides 64-130 of GDP1

<400> SEQUENCE: 16
agttcctctt ctgtttcttt gaaggctgcc gaaaagcctt tcaaggttac tgtgattgga      60
tctggta                                                                67

<210> SEQ ID NO 17
<211> LENGTH: 67
<212> TYPE: DNA
<213> ORGANISM: Artificial Sequence
<220> FEATURE:
<223> OTHER INFORMATION: Nucleotides 64-130 of GDP1 with mutation
```

```
<220> FEATURE:
<221> NAME/KEY: misc_feature
<222> LOCATION: (45)..(47)
<223> OTHER INFORMATION: these nucleotides are mutated

<400> SEQUENCE: 17
agttcctctt ctgtttcttt gaaggctgcc gaaaagcctt tcaagtaaac tgtgattgga    60
tctggta                                                             67

<210> SEQ ID NO 18
<211> LENGTH: 68
<212> TYPE: DNA
<213> ORGANISM: Artificial Sequence
<220> FEATURE:
<223> OTHER INFORMATION: Nucleotides 145-212 of GDP2

<400> SEQUENCE: 18
atgactgctc atactaatat caaacagcac aaacactgtc atgaggacca tcctatcaga    60
agatcgga                                                            68

<210> SEQ ID NO 19
<211> LENGTH: 68
<212> TYPE: DNA
<213> ORGANISM: Artificial Sequence
<220> FEATURE:
<223> OTHER INFORMATION: Nucleotides 145-212 of GDP2 with mutation
<220> FEATURE:
<221> NAME/KEY: misc_feature
<222> LOCATION: (46)..(48)
<223> OTHER INFORMATION: these nucleotides are mutated

<400> SEQUENCE: 19
atgactgctc atactaatat caaacagcac aaacactgtc atgagtaaca tcctatcaga    60
agatcgga                                                            68
```

RECOMBINANT YEAST FOR PRODUCING 2,3-BUTANEDIOL INCLUDING PYRUVATE DECARBOXYLASE DERIVED FROM CANDIDA TROPICOLIS AND METHOD FOR PRODUCING 2,3-BUTANEDIOL USING THE SAME

SEQUENCE LISTING

The Sequence Listing submitted in text format (.txt) filed on Dec. 1, 2020, named "SequenceListing.txt", created on Dec. 1, 2020 (17.1 KB), is incorporated herein by reference.

BACKGROUND OF THE INVENTION

Field of the Invention

The present invention relates to a recombinant yeast for producing 2,3-butanediol that can produce acetyl-CoA required for growth, while minimizing production of ethanol, which is a by-product during production of 2,3-butanediol, by introducing, into the cells, pyruvate decarboxylase derived from *Candida tropicolis*, which is lower in activity than its own pyruvate decarboxylase, and a method for producing 2,3-butanediol using the same.

The present invention relates to a method for producing 2,3-butanediol and more particularly, to a method for producing 2,3-butanediol that can inhibit production of glycerol, which is a by-product of production of 2,3-butanediol.

Description of the Related Art 2,3-butanediol is a chemical substance used in the synthesis of main ingredients constituting solvents, anti-freeze agents, plasticizers, pharmaceuticals and cosmetics, and is a biochemical material used as a precursor of 1,3-butadiene for the production of methyl ethyl ketone (MEK), which is a liquid fuel additive, and for the synthesis of styrene-butadiene rubber (SBR), which is a raw material for automobile tires.

In order to produce 2,3-butanediol using biological methods, it is necessary to develop 2,3-butanediol strains and develop optimal fermentation processes by metabolic engineering methods. In particular, it is necessary to develop strains having excellent safety for mass production of 2,3-butanediol, and having high yield and excellent productivity for commercialization thereof.

Meanwhile, conventional strains used for the production of 2,3-butanediol include *Klebsiella oxytoca, Klebsiella pneumoniae, Aerobacter aerogenes, Bacillus subtilis, Paenibacillus polymyxa, Serratia marcescens* and the like.

However, although these strains can produce 2,3-butanediol with high yield and excellent productivity, they were classified as pathogenic microorganisms and had inherent limitations in safety and industrialization. Thus, methods for producing 2,3-butanediol using yeasts well-known as GRAS microorganisms have been conventionally developed. However, these yeasts have the following limitations in industrial use as 2,3-butanediol-producing strains.

In the prior art, yeast strains, from which the core gene, pyruvate decarboxylase (PDC), was removed, were used in order to prevent conversion of pyruvate, which is a main precursor of 2,3-butanediol, into ethanol. 2,3-butanediol could be successfully produced at a high yield from this yeast strain of 2,3-butanediol by introducing a 2,3-butanediol biosynthesis pathway, but, disadvantageously, cell growth and substrate consumption rates were remarkably decreased due to removal of the PDC enzyme and productivity of 3-butanediol was thus remarkably low.

Therefore, low cell growth rate and low substrate consumption rate of conventional strains have to be solved in order to commercially produce 2,3-butanediol using yeasts.

The technology for producing biochemical materials refers to a method for producing raw materials of various chemicals and polymers using biomass as a raw material.

2,3-butanediol is a material that can be converted into 1,3-butadiene, which is a synthetic rubber as a raw material of automobile tires. In addition, 2,3-butanediol can also be used for the production of methyl ethyl ketone (MEK) as a liquid fuel additive through dehydrogenation. In addition, 2,3-butanediol can be converted into a material used for pharmaceuticals, cosmetics and the like through esterification.

When 2,3-butanediol is intended to be produced by biological methods, it is necessary to develop a strain for producing 2,3-butanediol using a metabolic engineering technique and a fermentation process using the same. In particular, it is necessary to develop strains which can be produced with high yield, productivity and purity for industrial and economic production of 2,3-butanediol.

Production of 2,3-butanediol through microbial fermentation is mainly carried out by a method using bacterial strains such as *Klebsiella oxytoca, Klebsiella pneumoniae* and *Bacillus subtilis*. However, most of these bacterial strains are classified as pathogenic microorganisms and thus have limitations in safety and industrialization.

Accordingly, recently, methods for producing 2,3-butanediol using GRAS microorganisms (yeasts) have been developed. In accordance with such a method, 2,3-butanediol was successfully produced at high concentration by removing the core gene, pyruvate decarboxylase, or regulating the expression level thereof and introducing the 3-butanediol biosynthetic pathway, in order to prevent production of ethanol from yeasts and facilitate production of 2,3-butanediol.

However, the strain for producing 2,3-butanediol has problems in that it involves production of glycerol as a by-product involved in production of 2,3-butanediol, and causes the glycerol present as the fermentation product to entail additional purification process costs.

Therefore, there is a need for development of 2,3-butanediol-producing strains with inhibitory activity against production of glycerol in order to produce 2,3-butanediol more economically and commercially.

SUMMARY OF THE INVENTION

Therefore, the present invention has been made in view of the above problems, and it is one object of the present invention to develop and provide a method for producing 2,3-butanediol with excellent productivity by solving low cell growth and low substrate consumption rates of conventional 2,3-butanediol-producing strains.

It is another object of the present invention to develop and provide a method for producing 2,3-butanediol with high purity and excellent productivity, while inhibiting production of glycerol, which is a by-product obtained during production of 2,3-butanediol.

In accordance with the present invention, the above and other objects can be accomplished by the provision of recombinant *Saccharomyces cerevisiae* for producing 2,3-butanediol, transformed so as to lose functions of pyruvate decarboxylase of *Saccharomyces cerevisiae*, transformed so as to express pyruvate decarboxylase derived from *Candida tropicalis*, transformed so as to express acetolactate synthase, transformed so as to express acetolactate decarboxylase, and transformed so as to express butanediol dehydrogenase. For example, the pyruvate decarboxylase derived from *Candida tropicalis* may include an amino acid sequence set forth in SEQ ID NO: 2.

The yeast strain for producing 2,3-butanediol according to the present invention can synthesize acetyl-CoA, while avoiding production of ethanol, by introducing *Candida tropicalis*-derived Pdc, which is less active than its own pyruvate decarboxylase (Pdc), into the cells of the strain, thereby increasing the strain growth rate and the substrate consumption rate and ultimately greatly improving productivity of 2,3-butanediol.

Meanwhile, the transformation of the recombinant *Saccharomyces cerevisiae* for producing 2,3-butanediol according to the present invention, so as to lose the function of pyruvate decarboxylase, is for example carried out by partially disrupting the PDC1 gene encoding pyruvate decarboxylase 1 from the *Saccharomyces cerevisiae* strain or knocking out (entirely removing) the same therefrom, or by partially disrupting the PDC5 gene encoding pyruvate decarboxylase 5 from the *Saccharomyces cerevisiae* strain or knocking out the same therefrom, or by partially disrupting the PDC6 gene encoding pyruvate decarboxylase 6 from the *Saccharomyces cerevisiae* strain or knocking out the same therefrom.

The loss of enzyme activity can be achieved by partially disrupting the gene encoding the corresponding enzyme or by knocking out the gene. Partial disruption and knock-out of the gene can be easily accomplished using techniques well-known in the field of genetic engineering and a detailed description thereof will be omitted.

Meanwhile, the transformation of the recombinant *Saccharomyces cerevisiae* for producing 2,3-butanediol according to the present invention, so as to express pyruvate decarboxylase derived from *Candida tropicalis*, is carried out, for example, by introducing the PDC1 gene encoding pyruvate decarboxylase 1 derived from *Candida tropicalis* into the *Saccharomyces cerevisiae* strain. As can be seen from the experiment of the present invention, the activity of pyruvate decarboxylase 1 derived from *Candida tropicalis* was low enough to biosynthesize acetyl-CoA, while not producing ethanol, so that cell growth and glucose consumption rates were high.

Meanwhile, the PDC1 gene derived from *Candida tropicalis* according to the present invention is preferably regulated by a glyceraldehyde phosphate dehydrogenase (GPD2) promoter. The GPD2 promoter may, for example, include the amino acid sequence of SEQ ID NO: 2.

In addition, it is preferable that one copy of the PDC1 gene derived from *Candida tropicalis* is preferably introduced into the strain. It can be seen from the following experiment that, when the GPD2 promoter was used and a single copy was introduced into the strain, cell growth and glucose consumption rates were high, ethanol was not produced and ultimately, productivity of 2,3-butanediol was high.

Meanwhile, in another aspect of the present invention, provided is a method for producing 2,3-butanediol including culturing the recombinant *Saccharomyces cerevisiae* according to the present invention. In this case, the culture is preferably carried out using a medium containing glucose. Glucose is a carbon source preferred for *Saccharomyces cerevisiae*. When glucose is used as a carbon source, the growth of the strain can be maximized and thus productivity can be increased.

Meanwhile, the method for producing 2,3-butanediol according to the present invention is preferably carried out, while supplying oxygen, because a large amount of ATP is produced through oxygen supply so that the growth of microorganisms can be promoted.

Meanwhile, the method for producing 2,3-butanediol according to the present invention is preferably carried out by fed-batch culture including continuously supplying glucose. That is, production of 2,3-butanediol can be maximized in one batch by continuously supplying a medium in a fed-batch manner.

In accordance with another aspect of the present invention, provided is recombinant *Saccharomyces cerevisiae* for producing 2,3-butanediol wherein all the GPD1 and GPD2 genes involved in glycerol biosynthesis are removed and genes encoding NADH oxidase are introduced. When all the GPD1 and GPD2 genes are removed and the genes encoding NADH oxidase are introduced, 2,3-butanediol can be produced with high purity, high yield and high productivity without producing glycerol, as can be seen from the experiments of the invention.

The *Saccharomyces cerevisiae* for producing 2,3-butanediol according to the present invention means *Saccharomyces cerevisiae* into which a pathway for production of 2,3-butanediol is introduced through various genetic manipulations and may be obtained using well-known strains already developed for this purpose (Ng et al., Production of 2,3-butanediol in *Saccharomyces cerevisiae* by in silico aided metabolic engineering, Microbial Cell Factories, 2012, 11:68). Preferably, the *Saccharomyces cerevisiae* is transformed so as to express acetolactate synthase, is transformed so as to express acetolactate decarboxylase, and is transformed so as to express butanediol dehydrogenase.

In this case, the transformation so as to express the acetolactate synthase is preferably carried out by introducing alsS, the gene encoding alpha-acetolactate synthase, the transformation so as to express acetolactate decarboxylase is preferably carried out by introducing alsD, the gene encoding alpha-acetolactate decarboxylase, and the transformation so as to express butanediol dehydrogenase is preferably carried out by overexpressing BDH1, the gene encoding 2,3-butanediol dehydrogenase possessed by *Saccharomyces cerevisiae*.

Meanwhile, the recombinant *Saccharomyces cerevisiae* according to the present invention is preferably *Saccharomyces cerevisiae* for producing 2,3-butanediol wherein the functions of pyruvate decarboxylase are lost and PDC1, the gene encoding pyruvate decarboxylase derived from *Candida tropicalis*, is introduced. More preferably, the function loss of the pyruvate decarboxylase is carried out by partially disrupting or knocking out one or more genes selected from PDC1, PDC5 and PDC6, genes encoding pyruvate decarboxylase. The gene PDC1 encoding pyruvate decarboxylase is preferably expressed in the presence of the GPD2 promoter.

By introducing pyruvate decarboxylase (Pdc) derived from *Candida tropicallis*, which is less ehsactive than pyruvate decarboxylase (Pdc) possessed by *Saccharomyces cerevisiae*, into the microorganism, synthesis of acetyl-CoA is possible, while avoiding production of ethanol, so that the growth rate of the strain and the consumption rate of substrate can be increased, and ultimately the productivity of 2,3-butanediol can be greatly improved (see Korean Patent Application No. 10-2015-0124845).

Meanwhile, in the recombinant *Saccharomyces cerevisiae* according to the present invention, the NADH oxidase is preferably an NADH oxidase derived from *Lactobacillus lactis*.

In addition, in the recombinant *Saccharomyces cerevisiae* of the present invention, the gene encoding an NADH oxidase is preferably inserted into the p426GPD plasmid, which is a multi-copy plasmid, and the promoter of the TDH3 gene is preferably used as a promoter. The reason for this is that the activity of NADH oxidase was very high under these conditions.

Meanwhile, the present invention relates to a method for producing 2,3-butanediol including culturing recombinant *Saccharomyces cerevisiae* in a medium supplemented with glucose, wherein the recombinant *Saccharomyces cerevisiae* is transformed so as to express acetolactate synthase, is transformed so as to express acetolactate decarboxylase and is transformed so as to express butanediol decarboxylase, wherein the GPD1 gene and the GPD2 gene involved in glycerol biosynthesis are removed, and genes encoding NADH oxidase are introduced. According to the method for producing 2,3-butanediol according to the present invention, 2,3-butanediol can be produced with high purity, high yield and high productivity without production of glycerol, which is a by-product.

Meanwhile, the method for producing 2,3-butanediol according to the present invention is preferably carried out using the recombinant *Saccharomyces cerevisiae* wherein functions of pyruvate decarboxylase are lost and the gene PDC1 encoding pyruvate decarboxylase derived from *Candida tropicalis* is introduced.

Meanwhile, the method for producing 2,3-butanediol according to the present invention is preferably carried out while continuously supplying oxygen. The oxygen supply results in consumption of NADH and thus a decrease in concentration of NADH in the cytoplasm. That is, the removal of GPD1 and GPD2 enables NADH accumulated in the cytoplasm to be consumed. In this case, it is preferable that the continuous supply of oxygen is more preferably carried out by continuously feeding oxygen such that the amount of oxygen supplied in the middle stage of fermentation is lower than the amount of oxygen supplied in the initial stage of fermentation. In the initial stage of fermentation, since cell growth and the glucose consumption rates are high and thus the amount of NADH supplied to the cytoplasm is high, NADH should be consumed by supplying a large amount of oxygen. However, after the initial stage of fermentation, cell growth and the glucose consumption rates are high, thus reducing the amount of oxygen needed to consume NADH. In this case, when excess oxygen is supplied, acetoin, which is an oxidized form of 2,3-butanediol, may be accumulated as a by-product. For this reason, it is preferable to reduce the amount of oxygen after the initial stage of fermentation.

Meanwhile, in the method for producing 2,3-butanediol according to the present invention, it is preferable that the culture is preferably fed-batch culture including continuously supplying glucose. The production of 2,3-butanediol can be maximized by fed-batch culture.

BRIEF DESCRIPTION OF THE DRAWINGS

The above and other objects, features and other advantages of the present invention will be more clearly understood from the following detailed description taken in conjunction with the accompanying drawings, in which:

FIG. 14 shows a sequence of GPD1 genes, activity of which is removed, wherein the mutated site is underlined;

FIG. 15 shows a sequence of GPD2 genes, activity of which is removed, wherein the mutated site is underlined;

DETAILED DESCRIPTION OF THE INVENTION

The present invention focuses on development of a recombinant yeast for producing 2,3-butanediol at high productivity using a metabolic engineering method and production of 2,3-butanediol at high productivity from glucose using the recombinant yeast.

Figure 18:
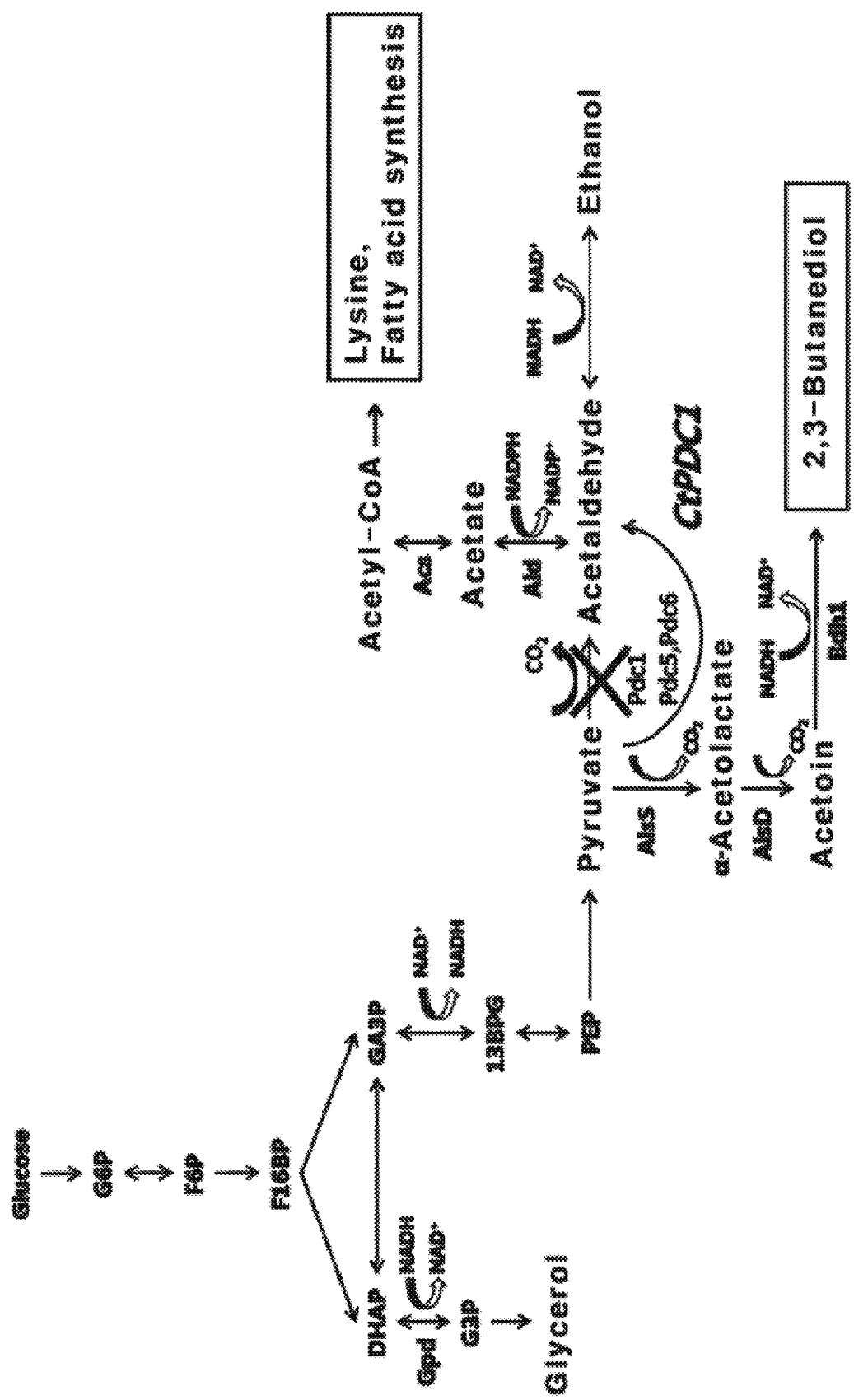
FIG. 18 shows the Reference Diagram which was prepared to show the result for the search for PDC genes with low activity.

In order to suitably control the activity of Pdc encoding the pyruvate decarboxylase enzyme, PDC genes with low activity were searched for. As a result, a strain for producing 2,3-butanediol with high yield was established by cloning the PDC1 (CtPDC1) gene derived from *Candida tropicalis*, that is, the nucleic acid sequence of SEQ ID NO: 1 and the amino acid sequence of SEQ ID NO: 2, and expressing a single copy of the same (see Reference Diagram, FIG. 18).

Hereinafter, the configuration of the present invention will be described in more detail with reference to the following examples. The scope of the present invention is not limited to the following examples and includes modifications of the technical concept equivalent thereto.

Production Example 1: Establishment of 2,3-Butanediol-Producing Strains into which Disruption of PDC1, PDC5 and PDC6 Genes and 2,3-Butanediol Biosynthetic Pathway are Introduced In case of wild yeast, pyruvate produced as a glucose metabolite is mostly converted into ethanol by pyruvate decarboxylase and alcohol dehydrogenase. Thus, it is necessary to prevent conversion of pyruvate into ethanol in order to produce 2,3-butanediol at high yield from yeast.

Thus, in the present invention, the pyruvate decarboxylase genes, PDC1, PDC5 and PDC6, were first disrupted to establish strains in which the activity of pyruvate decarboxylase is completely removed. In order to introduce the 2,3-butanediol biosynthetic pathway into this strain, acetolactate synthase (alsS) and acetolactate decarboxylase (alsD) derived from *Bacillus subtilis* were introduced into a plasmid containing the CYC1 terminator and the TDH3 promoter of *S. cerevisiae*, and 2,3-butanediol dehydrogenase (BDH1) of *S. cerevisiae* was introduced into a plasmid containing the TDH3 promoter and the CYC1 terminator (refer to Korean Patent Laid-Open No. 10-2015-0068581 filed by the present inventors).

Example 1: Search for Pyruvate Decarboxylase (PDC) Gene Having Low Activity (1) Introduction The yeast strain, from which the PDC genes were removed, showed a low productivity of 2,3-butanediol due to low cell growth rate and low substrate consumption rate.

Thus, in order to efficiently produce 2,3-butanediol, the activity of pyruvate decarboxylase was suitably regulated to secure a pyruvate substrate, which is a precursor of 2,3-butanediol, and at the same time, PDC genes with low activity were searched for to supply the C2 compound.

(2) Materials and Methods

A. Genes and Plasmids

After extraction of the genomic DNAs from *Candida tropicalis*, *Kluyveromyces marxianus* and *Saccharomyces cerevisiae*, PDC1 (ScpDC1) derived from *Candida tropicalis*, PDC1 (KmPDC1) derived from *Kluyveromyces marxianus*, and PDC1 (ScPDC1), PDC5 (ScPDC5) and PDC6 (ScPDC6) genes derived from *Saccharomyces cerevisiae* were cloned.

As an expression vector for yeast, the "origin" of "2 micron plasmid" and the p426GPD plasmid containing a TDH3 promoter and a CYC1 terminator derived from *S. cerevisiae* were used.

The PDC gene fragment obtained by PCR was ligated to restriction sites of XmaI and XhoI of the p426GPD plasmid to establish a recombinant vector.

B. Transformation of Yeast

The established recombinant vector was introduced into the PDC1, PDC5 and PDC6-removed yeast strain of Production Example 1 by transformation.

(3) Result

The "in vitro enzyme activity" of the transformed yeast strain was measured to calculate the kinetic constant value of "$K_m$" or "$V_{max}$" from the activity values of the various concentrations of the substrate. The values are shown in Table 1 below.

TABLE 1

| Strain | CtPDC1 | KmPDC1 | ScPDC1 | ScpPDC5 | ScPDC6 |
|---|---|---|---|---|---|
| $K_m$ (mM) | 2.7 | 7.7 | 4.7 | 9.9 | 8.2 |
| $V_{max}$ (mU/mg protein) | 107 | 383 | 541 | 437 | 415 |

Test results showed that the activity of the CtPDC1 strain was significantly low, as compared to other Pdc strains. It was considered that control of Pdc activity necessary for optimizing the production of 2,3-butanediol would be possible with the use of strain CtPDC1 with low activity.

Example 2: Measurement of Cell Growth, Glucose Consumption Rate and 2,3-Butanediol Productivity of Strains Expressing CtPDC1 and KmPDC1

(1) Introduction

Cell growth and glucose consumption rates were measured using the Pdc-expressing strains (CtPDC1, KmPDC1) prepared in Example 1, and the productivities of 2,3-butanediol were compared.

(2) Materials and methods

A. Strains and Plasmids

A strain producing 2,3-butanediol, while not expressing Pdc, a strain expressing CtPDC1 and a strain expressing KmPDC1 were used. CtPDC1 and KmPDC1 were expressed using the TDH3 promoter and the CYC1 terminator of *S. cerevisiae*.

B. Medium and Culture Conditions

A medium containing 6.7 g/L of "yeast nitrogen base w/o nitrogen base", 1.4 g/L of "an amino acid mixture" and 80 g/L of glucose was used for fermentation. The initial cell concentration was 0.2 g/L, the fermentation temperature was maintained at 30° C. and the stirring speed was 80 rpm.

(3) Result

The control group with no PDC expression had a glucose consumption rate per hour of 0.10 g/L/h, while the CtPDC1-expressing strain had a glucose consumption rate per hour of 0.94 g/L/h, and the KmPDC1-expressing strain had a glucose consumption rate per hour of 1.09 g/L/h.

The strain not expressing PDC had a maximum dry cell concentration of 0.2 $g_{DCW}$/L, while the strain expressing CtPDC1 had a maximum dry cell concentration of 2.7 $g_{DCW}$/L and the strain expressing KmPDC1 had a maximum dry cell concentration of 2.8 $g_{DCW}$/L.

Meanwhile, the 2,3-butanediol and ethanol yields of the strain not expressing PDC were 0.259 $g_{2,3\text{-}butanediol}/g_{glucose}$ and 0 $g_{ethanol}/g_{glucose}$, respectively, the 2,3-butanediol and ethanol yields of the strain expressing CtPDC1 was 0.185 $g_{2,3\text{-}butanediol}/g_{glucose}$ and 0.185 $g_{ethanol}/g_{glucose}$, respectively, and the 2,3-butanediol and ethanol yields of the strain expressing KmPDC1 was 0.134 $g_{2,3\text{-}butanediol}/g_{glucose}$ and 0.275 $g_{ethanol}/g_{glucose}$, respectively.

Figure 1:
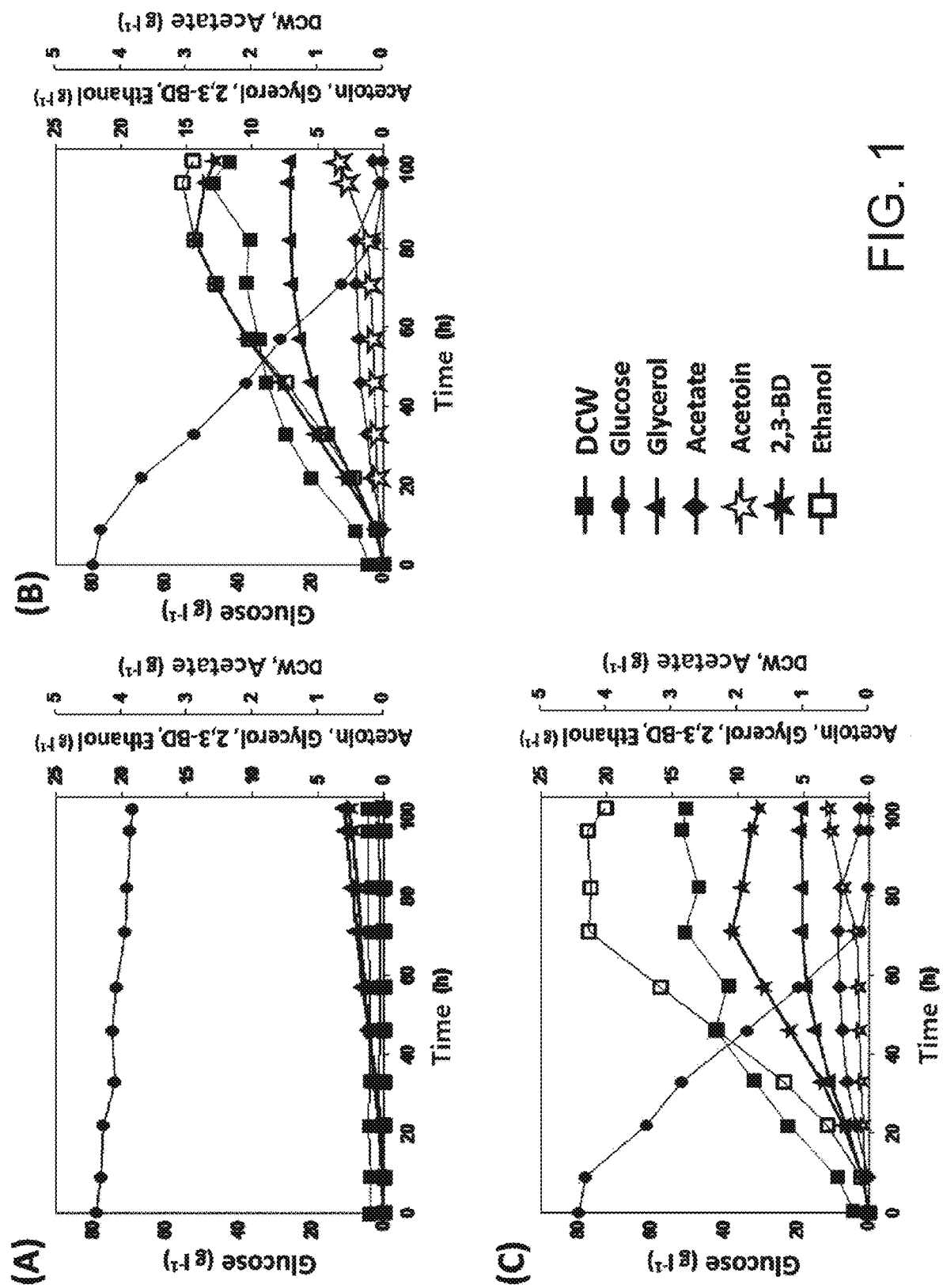
FIG. 1A is a graph showing a result of fermentation with a strain that produces 2,3-butanediol (control group) while not expressing PDC.
FIG. 1B is a graph showing a result of fermentation of the strain expressed by CtPDC1.
FIG. 1C is a graph showing a result of fermentation of the strain expressed by KmPDC1.

Meanwhile, the 2,3-butanediol productivity of the strain not expressing PDC was 0.026 $g_{2,3\text{-}butanediol}$/L/h, the 2,3-butanediol productivity of the strain expressing CtPDC1 was 0.175 $g_{2,3\text{-}butanediol}$/L/h, and the 2,3-butanediol productivity of the strain expressing KMPDC1 was 0.147 $g_{2,3\text{-}butanediol}$/L/h From the above experiments, it could be confirmed that the expression of PDC in the PDC-deficient 2,3-butanediol-producing strain resulted in significant increases in cell growth and glucose consumption rates, and a great increase in productivity (FIG. 1). FIG. 1A is a graph showing a result of fermentation with a strain producing 2,3-butanediol, while not expressing PDC (control group). FIG. 1B is a graph showing a result of fermentation of the strain expressed by CtPDC1. FIG. 1C is a graph showing a result of fermentation of the strain expressed by KmPDC1.

Example 3: Strain Establishment Having Various Expression Conditions of Pyruvate Decarboxylase Derived from *Candida tropicalis* and "In Vitro Activity Assay"

(1) Introduction

Since the expression level of PDC directly affects the yield and productivity of 2,3-butanediol, optimal CtPDC1 expression strains were established to select optimal CtPDC1 expression strains.

(2) Materials and Methods

A. Establishment of plasmids having various promoters

The PDC1 gene (CtPDC1) derived from *C. tropicalis* was amplified and inserted into each expression vector (using a CYC1 promoter, a GPD2 promoter-SEQ ID NO: 3, a TDH3 promoter as a promoter, and a CYC1 terminator as a terminator, respectively), and thereby transformed to establish a recombinant yeast strain. The strain to be used for transformation was a strain obtained when the OD value became 3 after being cultured in YNB medium for 2 days.

B. Transformation

Transformation was carried out using a LiAc method, and strains were selected in YNB leu-his-trp-ura-plate medium after transformation. As a result, a strain (BD5_C1CtPDC1) expressed by the CYC1 promoter and a single copy, a strain (BD5_G1CtPDC1) expressed by the GPD2 promoter and a single copy, a strain (BD5_C2CtPDC1) expressed by the CYC1 promoter and multiple copies, and a strain (BD5_T2CtPDC1) expressed by the TDH3 promoter and multiple copies were established.

(3) Results

Figure 2:
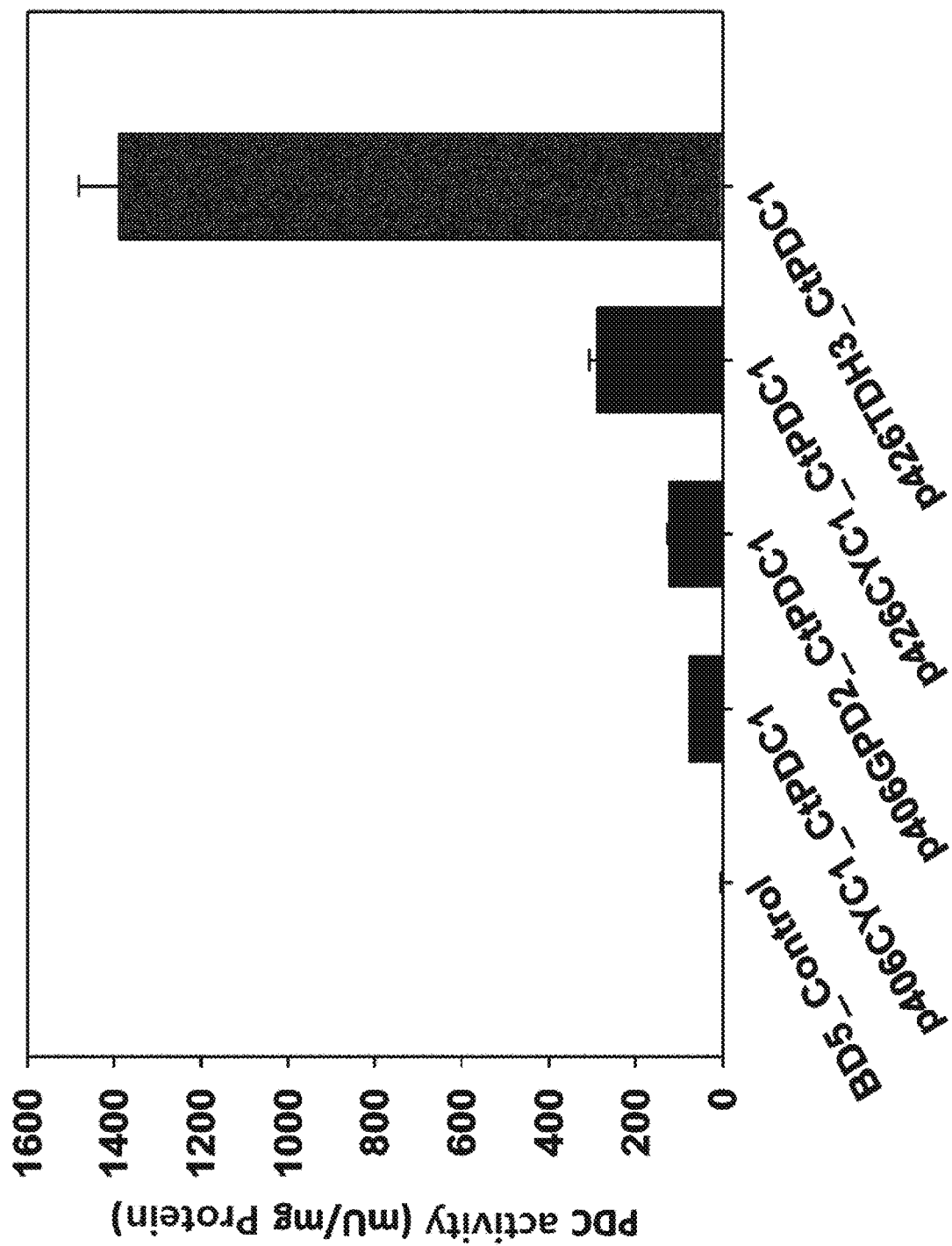
FIG. 2 shows a result of measurement of a Pdc titer of a strain expressing pyruvate decarboxylase derived from *Candida tropicalis* under various expression conditions (type of promoter and the number of copies)

In order to determine the PDC expression levels of these strains, "in vitro Pdc activity assay" was performed. As a result, the control group did not show a Pdc titer, while the established strains showed various Pdc expression levels (FIG. 2). FIG. 2 shows a result of Pdc titration of a strain expressing pyruvate decarboxylase derived from *Candida tropicalis*.

(3) Results

In order to determine the PDC expression levels of these strains, "in vitro Pdc activity assay" was performed. As a result, the control group did not show a Pdc titer, while the established strains showed various Pdc expression levels (FIG. 2). FIG. 2 shows a result of Pdc titration of a strain expressing pyruvate decarboxylase derived from *Candida tropicalis*.

Example 4: Production of 2,3-Butanediol Using Strain Expressing Pyruvate Decarboxylase Derived from *Candida Tropicalis*

(1) Introduction

In order to determine the fermentation behaviors of the 2,3-butanediol of the strains established in Example 3, fermentation experiments were performed in a YNB medium containing 90 g/L of glucose in the initial stage. As a control group, a strain transformed with a "p426GPD empty vector with no CtPDC1" was used.

(2) Fermentation Method

The initial strain inoculation concentration was 0.2 g/L, the fermentation temperature was maintained at 30° C., and the stirring speed of 80 rpm was maintained in a glass flask.

(3) Results

For the control group, 2,3-butanediol yield was 0.292 $g_{2,3\text{-}butanediol}/g_{glucose}$ and no ethanol was produced.

Figure 3:
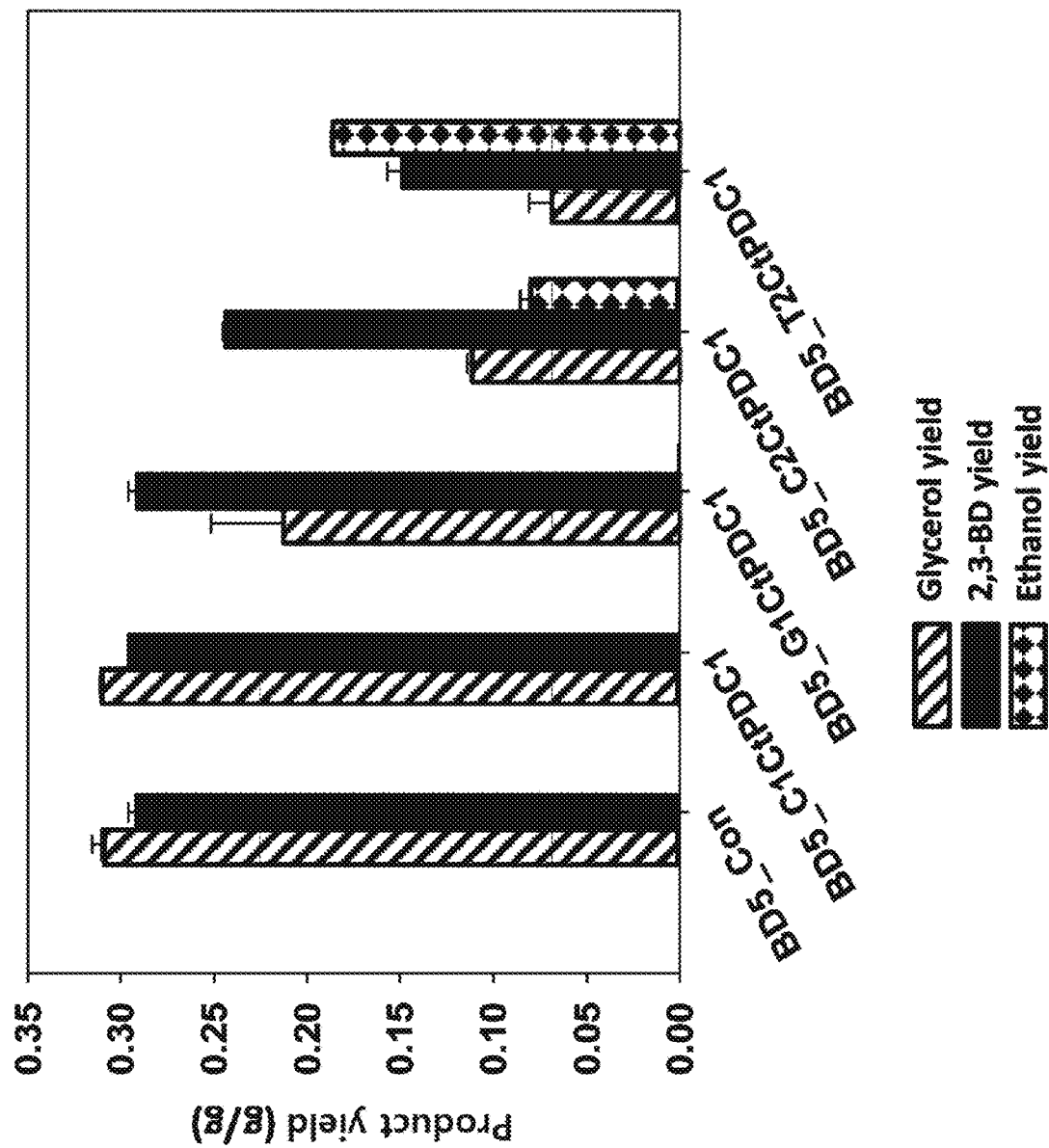
FIG. 3 is a graph showing yields of products (ethanol, glycerol and 2,3-butanediol) by PDC-expressing strains having various expression conditions.

In the BD5_C2CtPDC1 and BD5_T2CtPDC1 strains expressing multiple copies of PDC, a large amount of ethanol was produced, and the yields of 2,3-butanediol were decreased to 0.245 $g_{2,3\text{-}butanediol}/g_{glucose}$ and 0.150 $g_{2,3\text{-}butanediol}/g_{glucose}$ respectively (FIG. 3). FIG. 3 is a graph showing yields of products by the control group and PDC-expressing strains. FIG. 3 shows that BD5_C1CtPDC1 and BD5_G1CtPDC1 strains exhibit similar 2,3-butanediol production yields, but, non-preferably, BD5_C1CtPDC1 exhibits a high production yield of glycerol as a by-product. Therefore, it could be considered the BD5_G1CtPDC1 strain was more suitable as a 2,3-butanediol producing strain.

Figure 4:
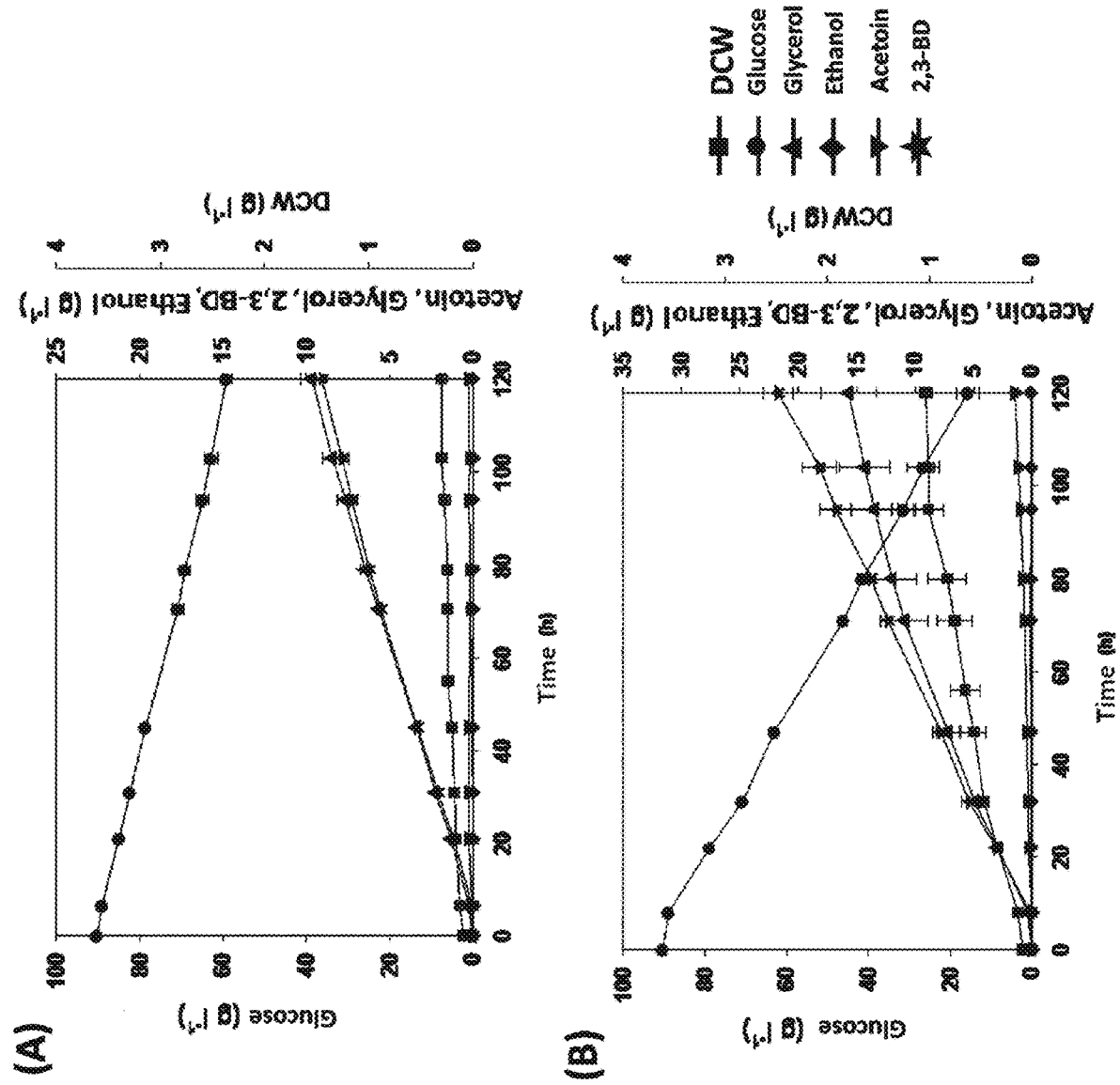
FIG. 4A is a graph showing a result of 2,3-butanediol fermentation by the control group for 120 hours
FIG. 4B is a graph showing a result of 2,3-butanediol fermentation by strain BD5 G1CtPDC1 for 120 hours.

Meanwhile, the PDC-expressing strain exhibited increased cell growth and glucose consumption rates. The glucose consumption rate per hour of the control group was 0.26 $g_{glucose}$/L/h, while the glucose consumption rate per hour of the BD5_G1CtPDC1 strain was 0.62 $g_{glucose}$/L/h. The BD5_G1CtPDC1 strain exhibited a similar 2,3-butanediol production yield to the control group, but the BD5_G1CtPDC1 strain exhibited an increased 2,3-butanediol productivity of 0.181 g/L/h, while the control group exhibited 2,3-butanediol productivity of 0.076 g/L/h (FIG. 4).

FIG. 4A is a graph showing a result of 2,3-butanediol fermentation by control group for 120 hours and FIG. 4B is a graph showing a result of 2,3-butanediol fermentation by BD5_G1CtPDC1 strain for 120 hours.

Example 5: Production of 2,3-Butanediol by Fed-Batch Culture (1) Introduction

In order to finally determine whether or not the BD5 G1CtPDC1 strain is suitable as a 2,3-butanediol-producing strain, fed-batch culture involving adding glucose during fermentation was performed.

(2) Materials and Methods

The medium used was YP medium (containing 10 g/L of yeast extract and 20 g/L of peptone), the initial glucose concentration was 270 g/L, and a 800 g/L glucose solution was added at the middle stage of fermentation. The initial cell concentration was 2 g/L, the fermentation temperature was maintained at 30° C., 0.5 vvm of air was injected and the stirring speed was maintained at 200 rpm.

Figure 5:
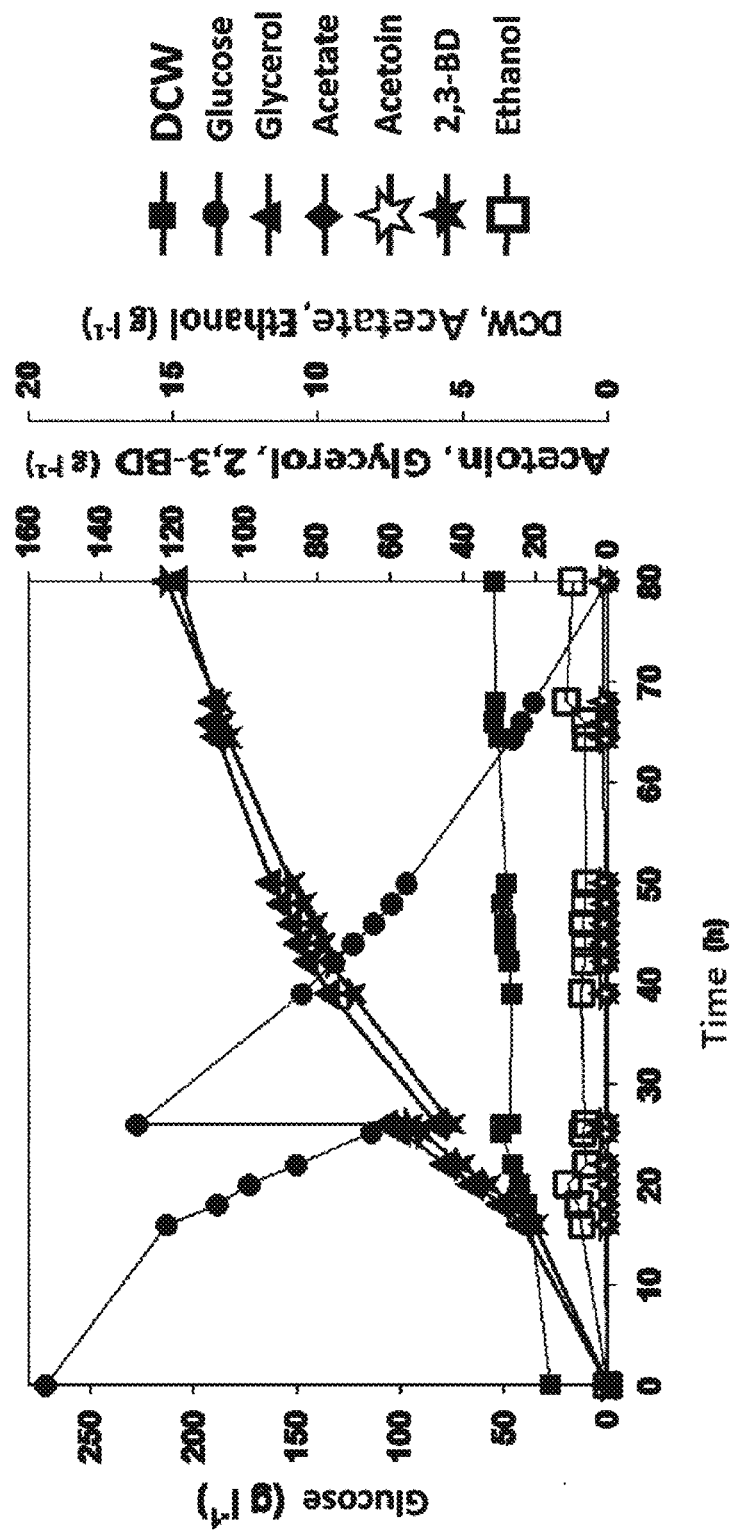
FIG. 5 is a graph showing a result of production of 2,3-butanediol by strain BD5_G1CtPDC1 measured by fed-batch culture.

(3) Results 121.8 g/L of 2,3-butanediol was produced for a culture time of 80 hours. At this time, the yield of 2,3-butanediol was 0.329 $g_{2,3\text{-}butanediol}/g_{glucose}$ and productivity was as high as 1.61 g/L/h (FIG. 5). FIG. 5 is a graph showing production results of 2,3-butanediol measured by fed-batch culture using the BD5_GlCtPDC1 strain.

From these results, it could be seen that the strain introduced with pyruvate decarboxylase derived from *Candida tropicalis* according to the present invention was suitable for the production of 2,3-butanediol.

The recombinant *Saccharomyces cerevisiae* strain for producing 2,3-butanediol is introduced with alpha-acetolactate synthase (alsS) and acetalactate decarboxylase (alsD) derived from *Bacillus subtilis*, in order to introduce a 2,3-butanediol biosynthesis pathway, and over-expresses the 2,3-butanediol dehydrogenase (BDH1) genes possessed by the yeast. In this regard, the present inventors developed, in addition to the basic 2,3-butanediol-producing strain, the strain ("BD5 strain") wherein PDC1, PDC5 and PDC6, pyruvate decarboxylase genes possessed by the *Saccharomyces cerevisiae* strain, are disrupted, and furthermore, developed the strain ("BD5_G1CtPDC1") into which the PDC1 gene encoding pyruvate decarboxylase derived from *Candida tropicalis*, which is less active than Pdc possessed thereby, is introduced (see Reference Diagram, FIG. 18).

Figure 19:
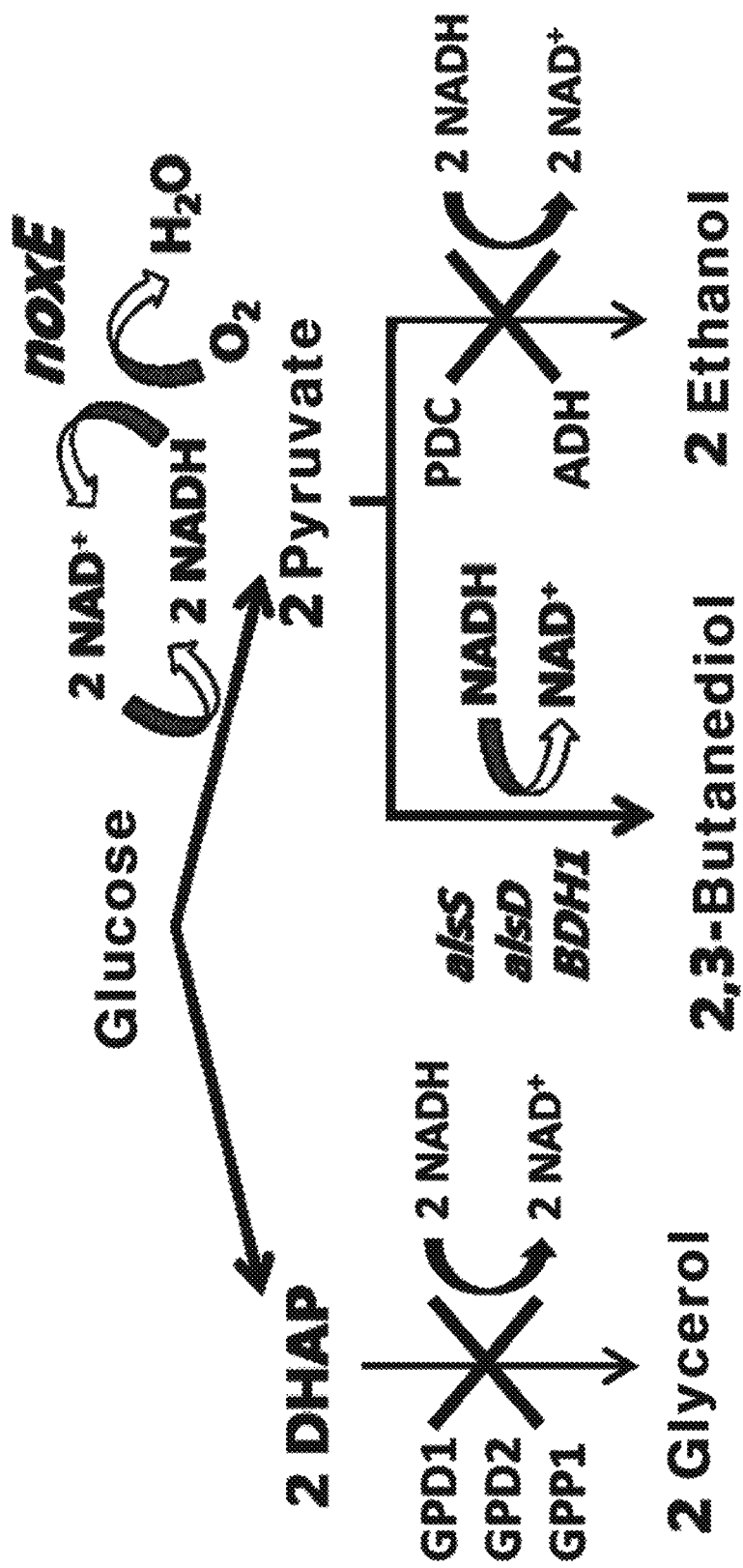
FIG. 19 shows the Reference Diagram which was prepared to show that by removing both GPD1 and GPD2 genes, 2,3-butanediol can be produced with high purity, high yield and high productivity, while completely inhibiting production of glycerol.

However, in the present invention, the NADH oxidase (NoxE) gene derived from *Lactobacillus lactis* was further expressed in the yeast strain for producing 2,3-butanediol, and glycerol-3-phosphate dehydrogenase (GPD1, GPD2) genes involved in glycerol biosynthesis were disrupted, to produce a yeast strain for producing 2,3-butanediol (Reference Diagram, FIG. 19).

When the GPD1 or GPD2 gene involved in glycerol biosynthesis is removed using NADH as a coenzyme, glycerol production may be reduced, but NADH is not consumed and accumulates in the cytoplasm. As a result, a problem occurs that the strain does not grow efficiently. However, according to the present invention, NADH can be consumed because NADH oxidase capable of oxidizing NADH is overexpressed.

Therefore, in the present invention, by removing both GPD1 and GPD2 genes, 2,3-butanediol can be produced with high purity, high yield and high productivity, while completely inhibiting production of glycerol (See Reference Diagram, FIG. 19).

Meanwhile, in the present invention, it was confirmed that the amount of oxygen supplied into the incubator can regulate the activity of the strain introduced with NADH oxidase established according to the present invention, and also affected the production of 2,3-butanediol. In addition, 2,3-butanediol production technology with high concentration, high yield and high productivity was developed through optimization of the culture process such as control of sugar concentration and oxygen supply.

Hereinafter, the configuration of the present invention will be described in more detail with reference to the following examples and test examples. The scope of the present invention is not limited to the following examples and test examples and includes modifications of the technical concept equivalent thereto.

Example 6: Production of Strain Expressing NADH Oxidase

A yeast strain for producing 2,3-butanediol was prepared through the previous study of the present inventors (Korean Patent Laid-open No. 10-2015-0068581, Korean Patent Application No. 10-2015-0124845) and this strain was used as a parent strain (strain "BD5") by the present inventors. The parent strain was obtained by removing the pyruvate decarboxylase (Pdc) genes, that is, PDC1, PDC5 and PDC6 from *S. cerevisiae* strain, and by introducing and reinforcing alpha-acetolactate synthase (AlsS) and alpha-acetolactate decarboxylase (AlsD) derived from *Bacillus subtilis*, and 2,3-butanediol dehydrogenase (Bdh1) derived from *Saccharomyces cerevisiae* so as to form a 2,3-butanediol biosynthetic pathway.

Meanwhile, production of plasmids for expression and gene cloning were performed in order to further introduce NADH oxidase into the parent strain. Five types of expression plasmids were produced for expression.

The CYC1 gene promoter, 289 bp, and the GPD2 gene promoter, 1144 bp, of *Saccharomyces cerevisiae* were inserted into the SacI and BamHI sites of the pRS406 (Mumberg et al., Yeast vectors for heterologous proteins in different genetic backgrounds. Gene 156 (1), 119-122) plasmid, which is a single copy plasmid, and the 655 bp TDD3 gene promoter of *Saccharomyces cerevisiae* was inserted into the SacI and XbaI sites thereof.

The NADH oxidase gene (SEQ ID NO: 4) cloned from the *Lactobacillus lactis* subsp. *cremoris* MG1363 strain by PCR was inserted into five types of expression plasmids in total (p406GPD2, p406TDH3, p426CYC1, p426GPD2, p426TDH3).

Five types of 2,3-butanediol-producing strains (BD5_p406GPD2_L1nox, BD5_p406TDH3_L1nox, BD5_p426CYC1_L1nox, BD5_p426GPD2_L1nox, BD5_p426TDH3_L1nox) expressing NADH oxidase were produced through such a process.

In addition, the pyruvate decarboxylase genes used in the prior art to increase the glucose consumption rate and cell growth rate of the Pdc-deficient yeast strain were introduced. For this purpose, NADH oxidase was expressed using, as a single copy plasmid, a TDH3 promoter having a resistant gene against aureobasidin A as an antibiotic, and a CYC1 terminator, and pyruvate decarboxylase (CtPDC1) derived from *Candida tropicalis* was expressed in the presence of the GPD2 promoter. The gene encoding pyruvate decarboxylase (CtPDC1) derived from *Candida tropicalis* is set forth in SEQ ID NO: 1.

Through the above process, strain BD5_Ctnox simultaneously expressing NADH oxidase and pyruvate decarboxylase could be established.

TABLE 2

Primers used for establishment of plasmids expressing NADH oxidase

| Primers | Restriction site | Sequence |
|---|---|---|
| Cloning of *S. cerevisiae* promoters | | |
| F_CYC1P | SacI | cGAGCTCatttggcgagcgttg (SEQ ID NO: 7) |
| R_CYC1P | BamHI | cgcGGATCCttagtgtgtgtatttgtg tttgc (SEQ ID NO: 8) |
| F_GPD2P | SacI | cGAGCTCcaaaaacgacatatctatta tagtg (SEQ ID NO: 9) |
| R_GPD2P | BamHI | cgcGGATCCctttgagtgcagttgtgt tt (SEQ ID NO: 10) |
| Cloning of *L. lactis* noxE | | |
| F_nox | BamHI | cgcGGATCCaaaatgaaaatcgtagtt atcggta (SEQ ID NO: 11) |

TABLE 2 -continued

Primers used for establishment of plasmids
expressing NADH oxidase

| Primers | Restriction site | Sequence |
|---|---|---|
| R_XhoI_nox | XhoI | ccgCTCGAGtttatttggcattcaaagct (SEQ ID NO: 12) |
| R_SalI_nox | SalI | acgcGTCGACtttatttggcattcaaagct (SEQ ID NO: 13) |

The CYC1 promoter is set forth in SEQ ID NO: 5, the GPD2 promoter is set forth in SEQ ID NO: 3, and the TDH3 promoter is set forth in SEQ ID NO: 6.

Example 7: In Vitro Enzyme Titration of Strain Expressing NADH Oxidase

The plasmid for expressing NADH oxidase produced in Example 6 was designed to have different activity. Thus, in vitro enzyme titers were measured to compare the expression levels of NADH oxidase in the produced strains.

About $1 \times 10^9$ exponential phase cells cultured in YNB medium (6.7 g/L, amino acid mixture 1.4 g/L) supplemented with 80 g/L of glucose and 0.5 g/L of ethanol were used.

After the intracellular enzymes were extracted using Yeast protein extraction reagent (Y-PER, Thermo Scientific, MA), the supernatant was used for the measurement of NADH oxidase. The measurement of NADH oxidase was carried out at 30° C. using a decreased absorbance at 340 nm through reaction in 50 mM potassium phosphate buffer containing 0.4 mM NADH and 0.3 mM EDTA (pH 7.0). Protein concentrations in crude extracts were measured by the Bradford method. 1 unit was expressed as 1 μmol of NADH oxidized per minute.

Figure 6:
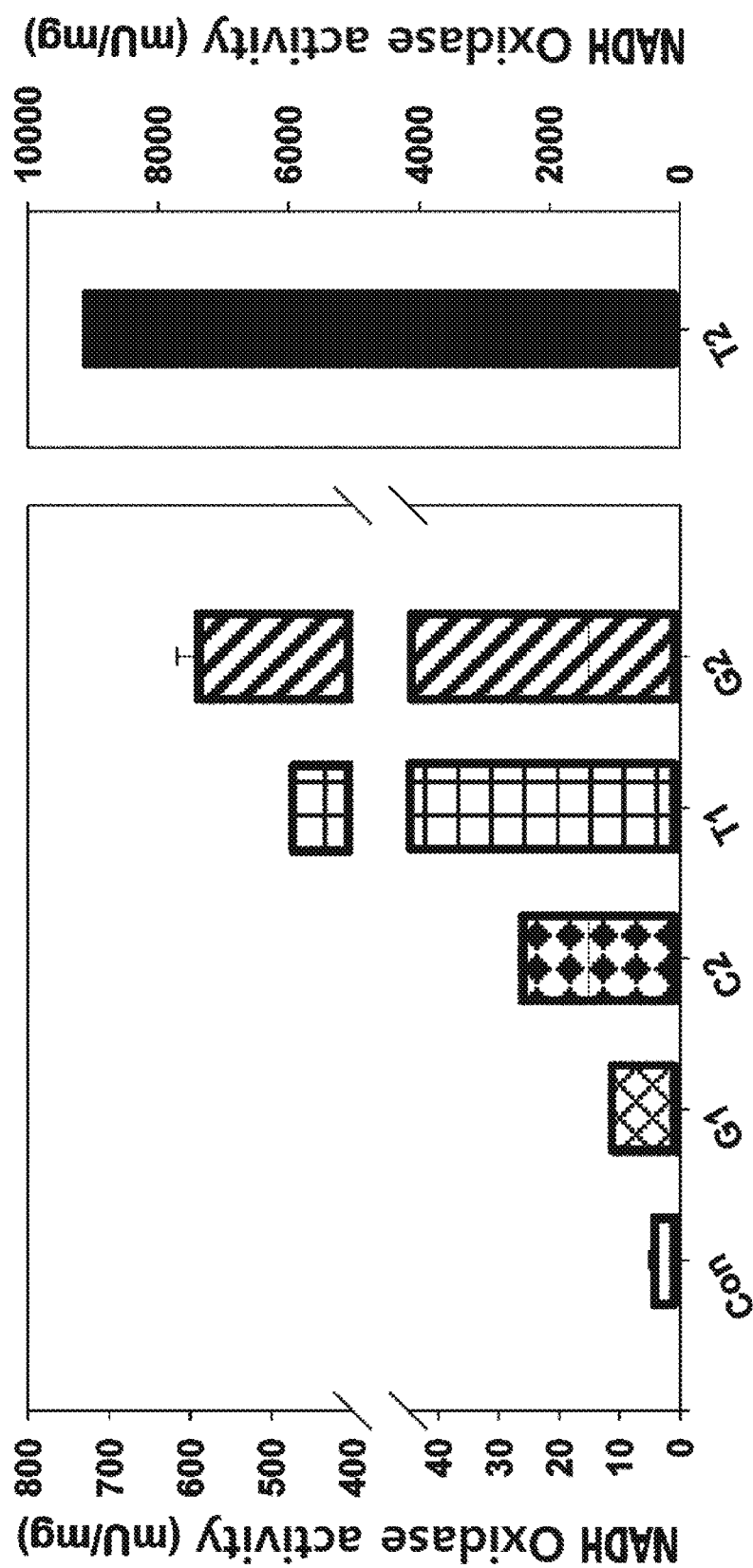
FIG. 6 shows results of in vitro titration of strains expressing NADH oxidase. Con: BD5_p426TDH3, G1: BD5_p406GPD2_L1nox, C2: BD5_p426CYC1_L1nox, T1: BD5_p406TDH3_L1nox, G2: BD5_p426GPD2_L1nox, T2: BD5p426TDH3_L1nox.

Test results show, as can be seen from FIG. 6, that the NADH oxidase activity varies depending on the type of promoter and the number of copies used for expression. The control group was transformed with a BD5 strain having the p426TDH3 vector inserted thereinto (Kim et al., expression of *Lactococcus lactis* NADH oxidase increases 2,3-butanediol production in Pdc-deficient *Saccharomyces cerevisiae*, Bioresource Technology 191 (2015) 512-519). The control group had an activity of 4.8 mU/mg protein, while the strain BD5_p406GPD2_L1nox had an activity of 11.2 mU/mg protein, and the strain BD5_p426TDH3_L1nox had an activity of 9153 mU/mg protein, which was 900 times higher than that of the strain BD5p406GPD2L1nox.

FIG. 6 shows the results of in vitro titration of strains expressing NADH oxidase. Con: BD5p426TDH3, G1: BD5_p406GPD2_L1nox, C2: BD5_p426CYC1_L1nox, T1: BD5_p406TDH3_L1nox, G2: BD5_p426GPD2_L1nox, T2: BD5_p426TDH3_L1nox.

Example 8: Determination of Change in Fermentation Behaviors of 2,3-Butanediol According to NADH Oxidase Activity When Pdc-deficient yeast strains for producing 2,3-butanediol produce 2,3-butanediol from sugars, NADH accumulates in the cytoplasm. In this regard, oxidation of NADH through respiration is limited, which results in production of excessive glycerol as a by-product.

Therefore, in the present invention, introduction of an additional pathway for oxidizing NADH was attempted by introduction of NADH oxidase. If such a prediction is successful, it is possible to reduce accumulation of glycerol as a by-product and increase production of 2,3-butanediol.

In order to identify this, batch fermentation experiments were conducted. The medium containing 80 g/L of glucose and 0.5 g/L of ethanol was used as YNB at the initial stage and the fermentation temperature was maintained at 30° C. Stirring was conducted at a rate of 80 rpm in 50 mL of a working volume in a 250 mL flask. The initial cell inoculation concentration corresponded to an optical density (OD) of 1.0 at a wavelength of 600 nm.

Figure 7:
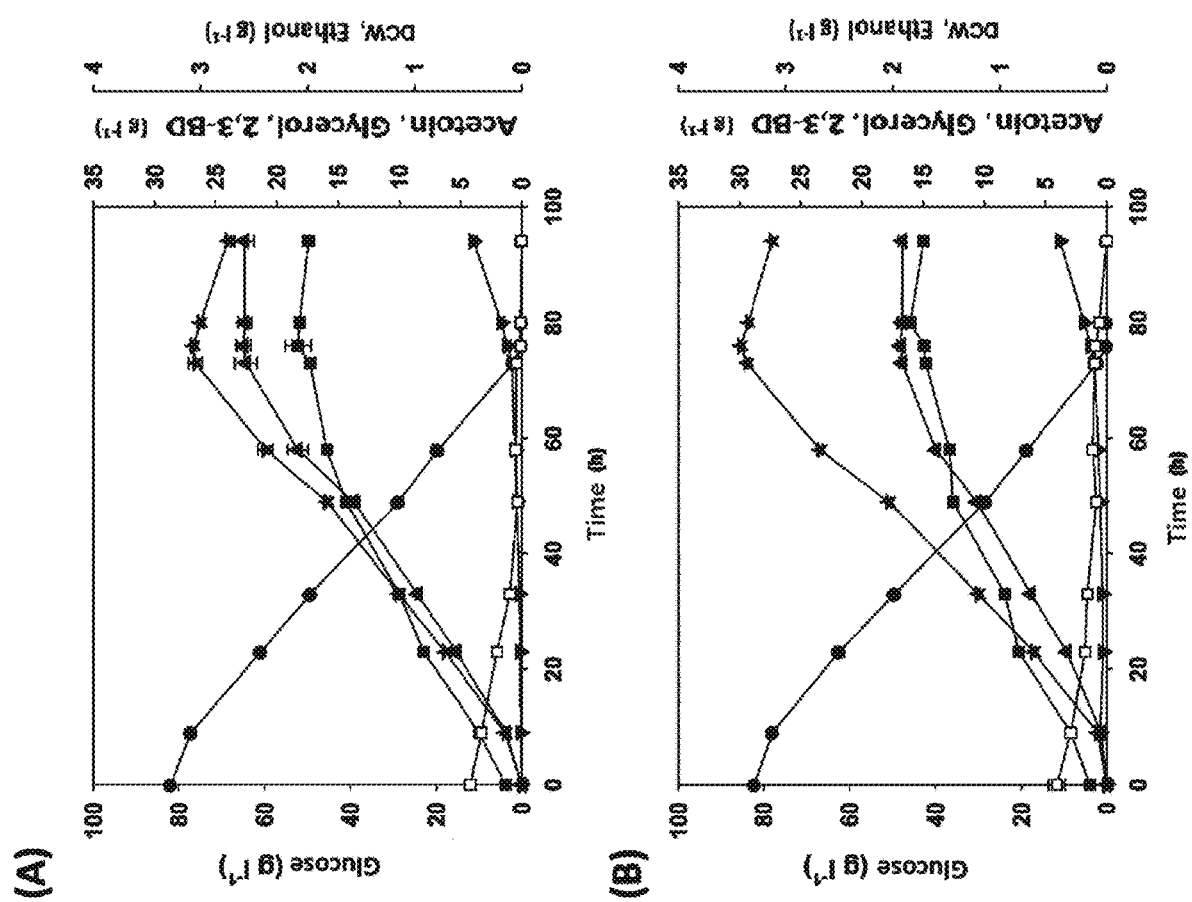
FIG. 7 shows a result of determination of change in fermentation behaviors of 2,3-butanediol by NADH oxidase-expressing strain through batch culture. A: BD5_p426TDH3 (control group), B: BD5p426TDH3L1nox.

The test results are shown in FIG. 7 and Table 3. Both the control and experimental groups perfectly consumed 80 g/L of glucose within about 76 hours. The control group had a glycerol production yield of 0.278 $g_{Glycerol}/g_{Glucose}$, while the strain BD5_p426TDH3_L1nox had a glycerol production yield of 0.209 $g_{Glycerol}/g_{Glucose}$. In addition, the control group had a 2,3-butanediol production yield of 0.332 $g_{2,3\text{-}butanediol}/g_{Glucose}$, while the BD5_p426TDH3_L1nox strain had an increased 2,3-butanediol production yield of 0.367 $g_{2,3\text{-}butanediol}/g_{Glucose}$. As such, through the expression of NADH oxidase, the production yield of glycerol was decreased and the production yield of 2,3-butanediol was increased. At this time, as the amount of NADH oxidase expression increased, the effect was improved.

FIG. 7 shows a result of determination of change in fermentation behaviors of 2,3-butanediol by NADH oxidase-expressing strain by batch culture. A: BD5_p426TDH3 (control group), B: BD5_p426TDH3_L1nox.

TABLE 3

Results of batch fermentation using strain expressing NADH oxidase

| Parameter* | Value (mean ± standard deviation) | | | | | |
|---|---|---|---|---|---|---|
| | BD5 _p426TDH3 | BD5 _p406GPD2 _L1nox | BD5_ p426CYC1 _L1nox | BD5 _p406TDH3 _L1nox | BD5 _p426GPD2 _L1nox | BD5 _p426TDH3 _L1nox |
| DCW (g/L) | 2.09 ± 0.10 | 1.93 ± 0.07 | 1.74 ± 0.11 | 1.55 ± 0.09 | 1.68 ± 0.04 | 1.69 ± 0.03 |
| $Y_{glycerol}$ (g/g) | 0.278 ± 0.011 | 0.266 ± 0.010 | 0.229 ± 0.001 | 0.231 ± 0.005 | 0.216 ± 0.009 | 0.209 ± 0.004 |
| $Y_{2,3\text{-}BD}$ (g/g) | 0.332 ± 0.000 | 0.338 ± 0.001 | 0.359 ± 0.000 | 0.359 ± 0.001 | 0.364 ± 0.003 | 0.367 ± 0.002 |
| $Y_{acetoin}$ (g/g) | 0.010 ± 0.001 | 0.009 ± 0.001 | 0.012 ± 0.001 | 0.011 ± 0.001 | 0.010 ± 0.000 | 0.012 ± 0.001 |

TABLE 3-continued

Results of batch fermentation using strain expressing NADH oxidase

| Parameter* | BD5 _p426TDH3 | BD5 _p406GPD2 _Llnox | BD5_ p426CYC1 _Llnox | BD5 _p406TDH3 _Llnox | BD5 _p426GPD2 _Llnox | BD5 _p426TDH3 _Llnox |
|---|---|---|---|---|---|---|
| $V_{glucose}$ (g/L · h$^{-1}$) | 1.10 ± 0.03 | 1.11 ± 0.02 | 1.06 ± 0.01 | 1.13 ± 0.00 | 1.07 ± 0.02 | 1.10 ± 0.00 |
| $P_{2,3\text{-}BD}$ (g/L · h$^{-1}$) | 0.364 ± 0.011 | 0.374 ± 0.008 | 0.381 ± 0.003 | 0.404 ± 0.002 | 0.391 ± 0.006 | 0.403 ± 0.002 |

Example 9: Determination of Change in Fermentation Behavior of 2,3-Butanediol by Oxygen Supply Difference The NADH oxidase used in this study reacts with NADH using oxygen as a substrate to produce water and NAD$^+$. Thus, it is possible to control the activity of NADH oxidase through the amount of oxygen supplied to the medium during fermentation, in addition to control of the expression level of NADH oxidase enzyme.

In this Example, the activity of NADH oxidase was changed according to the supply of oxygen, and a batch culture experiment was performed under different oxygen conditions in order to identify the effect of the NADH oxidase activity on the fermentation of 2,3-butanediol.

The medium used was a YP medium (yeast extract 10 g/L, peptone 20 g/L) supplemented with 90 g/L of glucose. The oxygen supply conditions were varied such that 25%, 50% and 100% air was introduced by mixing nitrogen with the air supplied into the medium. The fermentation temperature was maintained at 30° C., and air and a gas mixture of air/nitrogen were fed at 2 vvm and stirred at 500 rpm. A 1 L fermenter was used and the working volume was 500 mL. The strain BD5_Ctnox was used.

Figure 8:
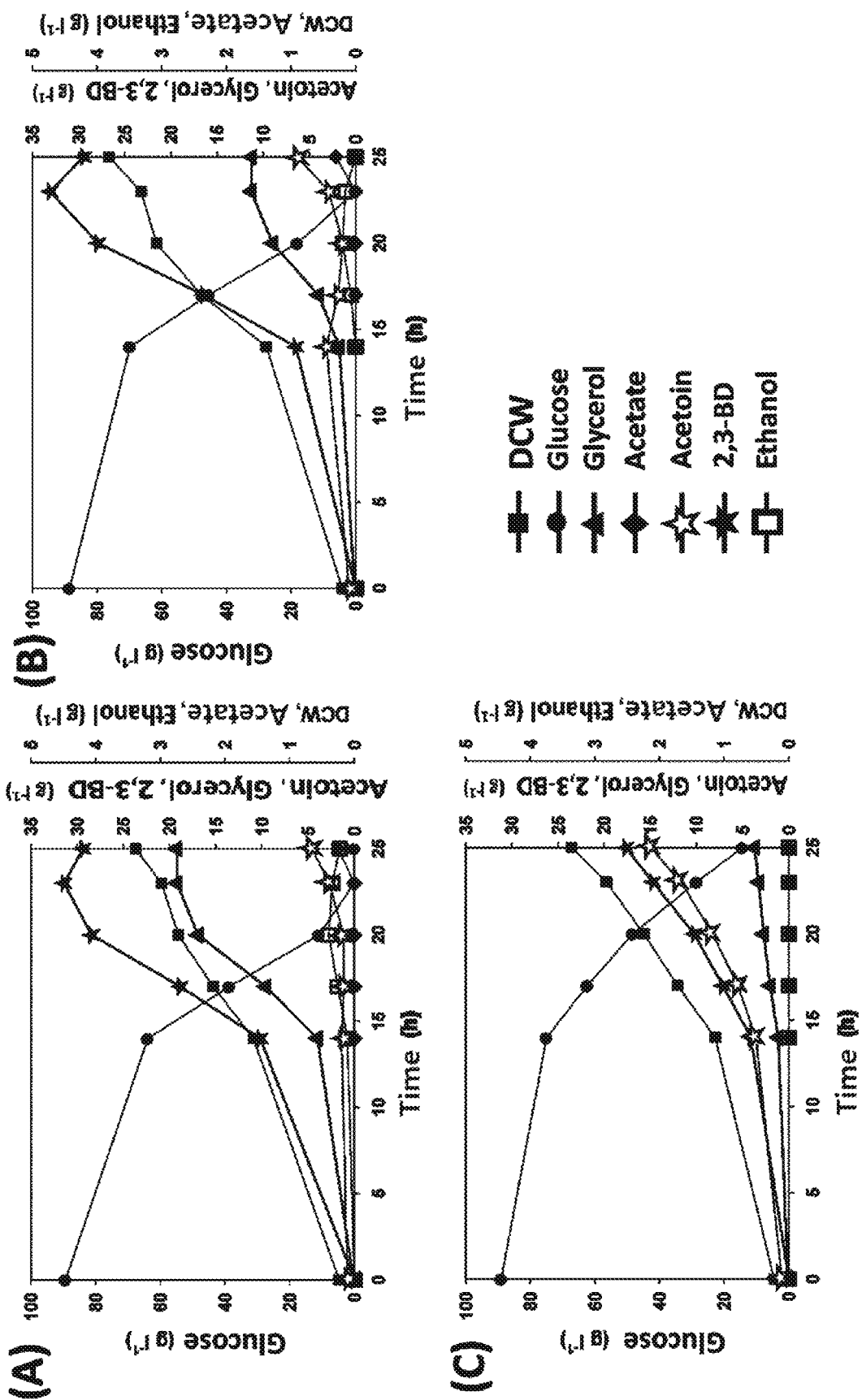
FIG. 8 shows a change in 2,3-butanediol fermentation behaviors by strain BD5_Ctnox depending on the amount of oxygen supplied. A) 25% air injection, B) 50% air injection, C) 100% air injection.

Test results are shown in Table 4 and FIG. 8. As shown in Table 8, the production behavior of 2,3-butanediol was changed according to the amount of oxygen supplied. As oxygen supply increased, glycerol production decreased and acetoin production increased. The production yield of 2,3-butanediol was the highest at 50% air. There was no significant difference in cell growth between the three conditions. However, the glucose consumption rate decreased under the condition of 100% air injection, as compared to under the other two conditions.

FIG. 8 shows a change in 2,3-butanediol fermentation behaviors of the BD5_Ctnox strain depending on the amount of oxygen supplied. A) 25% air injection, B) 50% air injection, C) 100% air injection.

Example 10: Measurement of Concentration Change in Intracellular NADH/NAD$^+$ Coenzymes Depending on Oxygen Supply Amount The concentrations of NADH and NAD$^+$ in the cells were measured using the 20-hour-old cells obtained in Example 9. About 4×10$^7$ cells were used for measurement and were measured using a kit for NAD$^+$/NADH measurement (Bio-Assay Systems, CA).

Figure 9:
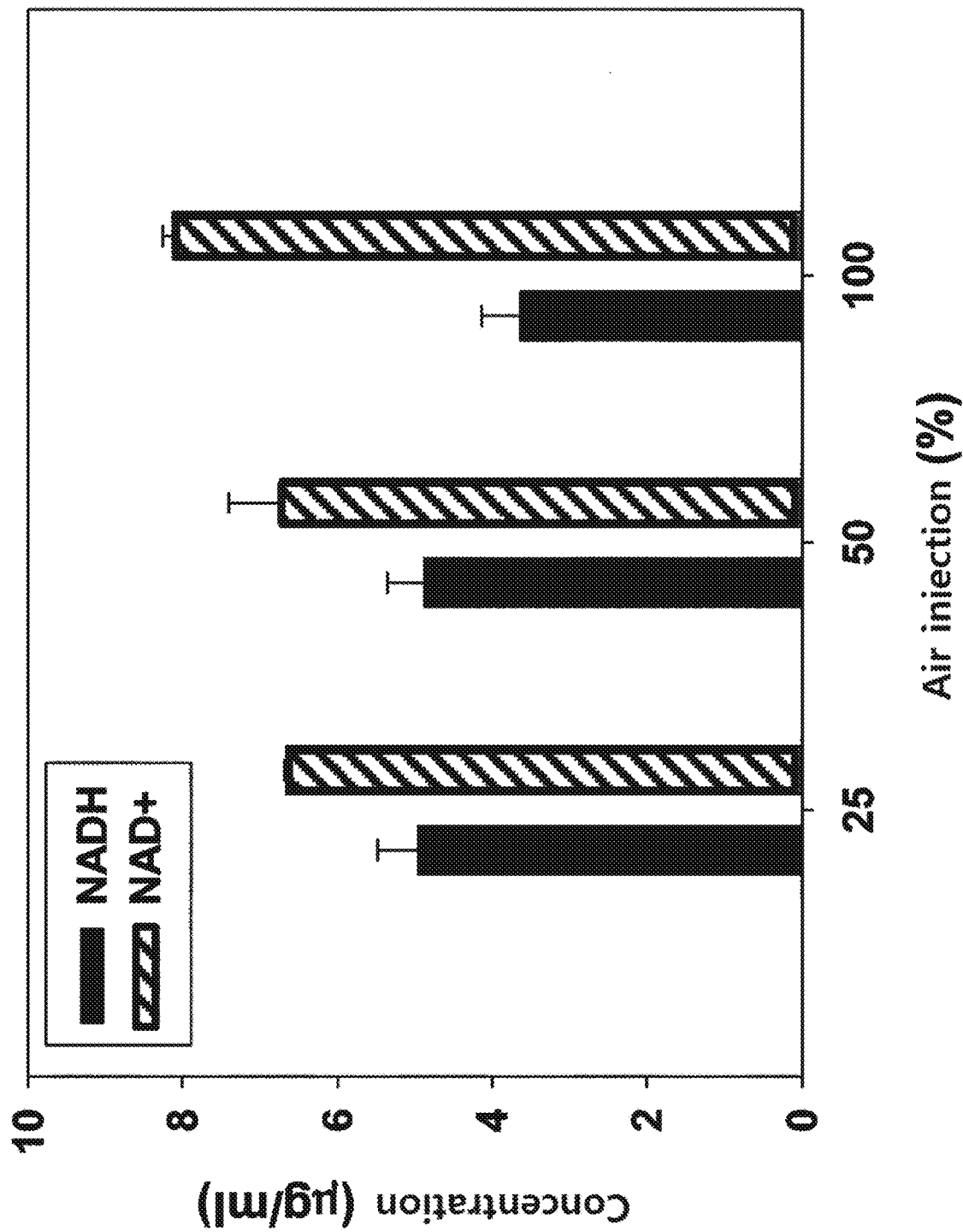
FIG. 9 shows a result of measurement of changes in concentrations of NADH and NAD$^+$, intracellular coenzymes, depending on oxygen supply amount.

Test results are shown in FIG. 9. As shown in FIG. 9, when the air ratio was 100%, the concentration of NADH decreased and the concentration of NAD+ increased. That is, as oxygen supply increased, the activity of intracellular NADH oxidase increased, which means that oxygen acts on NADH in the cells to directly oxidize NADH.

FIG. 9 shows a result of measurement of changes in concentrations of NADH and NAD$^+$, intracellular coenzymes, depending on oxygen supply amount.

Example 11: Fermentation of High-Concentration and High-Productivity 2,3-Butanediol by Controlling Oxygen Supply During Fed-Batch Culture In order to determine the availability of BD5_Ctnox strain as a strain for mass production of 2,3-butanediol, fed-batch culture was carried out by adding glucose during fermentation. The activity of NADH oxidase was regulated to reduce production of glycerol and the amount of oxygen fed during fermentation was converted in order to maximize production of 2,3-butanediol. YP medium was used as a medium, the initial glucose concentration was 330 g/L, and a 800 g/L glucose solution was added in the middle stage of fermentation. The initial cell inoculation concentration was 2.0 g/L and the fermentation temperature was maintained at 30° C. Oxygen was supplied under the conditions of 2 vvm and 500 rpm from the beginning to the middle of fermentation, and then oxygen was supplied at 1 vvm and 200 rpm. As a result, after the culture time of 78 hours, 154.3 g/L of 2,3-butane-

TABLE 4

Changes in 2,3-butanediol fermentation behaviors of BD5_Ctnox strain depending on oxygen supply

Figure 10:
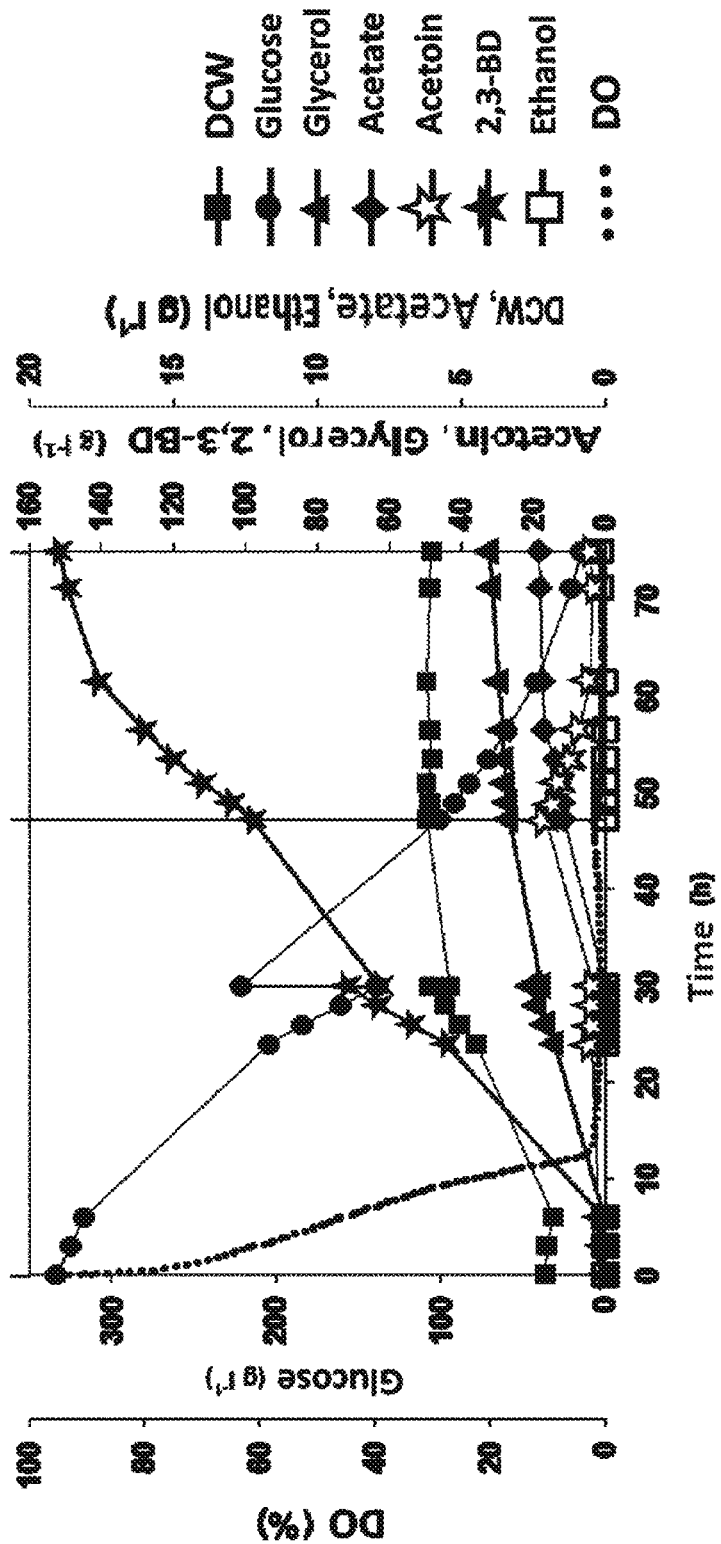
FIG. 10 is a fed-batch culture profile using strain BD5_Ctnox.

| Parameters | DCW$_{max}$ (g/L) | Glycerol (g/L) | Acetoin (g/L) | 2,3-BD (g/L) | Glycerol yield (g/g) | 2,3-BD Yield (g/g) | 2,3-BD productivity (g/L · h$^{-1}$) |
|---|---|---|---|---|---|---|---|
| 25% | 3.0 | 19.2 | 2.0 | 31.4 | 0.216 | 0.363 | 1.42 |
| 50% | 3.3 | 11.3 | 2.2 | 33.1 | 0.128 | 0.374 | 1.44 |
| 100% | 3.4 | 3.7 | 14.2 | 17.7 | 0.050 | 0.237 | 0.71 | diol was produced and the productivity was 1.98 $g_{2,3\text{-}Butanediol}$/L/h (see FIG. 10 and Table 5). At this time, the 2,3-butanediol production yield was 0.404 $g_{2,3\text{-}Butanediol}$/$g_{Glucose}$.

FIG. 10 is a fed-batch culture profile using strain BD5_Ctnox.

TABLE 5

Results of fedbatch culture profile using strain BD5_Ctnox.

| Parameters | DCW$_{max}$ (g/L) | Glucose consumed (g/L) | Glycerol (g/L) | 2,3-BD (g/L) | Ethanol (g/L) | Glycerol yield (g/g) | 2,3-BD yield (g/g) | 2,3-BD productivity (g/L · h$^{-1}$) |
|---|---|---|---|---|---|---|---|---|
| BD5_Ctnox | 6.2 | 404.3 | 32.5 | 154.3 | 0.1 | 0.088 | 0.404 | 1.98 |

Example 12: Preparation of Strain for Producing 2,3-Butanediol from which GPD1 and GPD2 are Removed Glycerol-3-phosphate dehydrogenase (Gpd) in *Saccharomyces cerevisiae* is a key metabolic enzyme for glycerol production, which is expressed by the GPD1 and GPD2 genes.

In the present invention, a recombinant yeast strain for producing 2,3-butanediol, from which the GPD1 and GPD2 genes were completely removed, was established in order to completely inhibit production of glycerol during 2,3-butanediol production. For this purpose, the Cas9-CRISPR method was applied and GPD1 and GPD2 genes was inactivated by converting the codons in the middle of ORF of the GPD1 and GPD2 genes, to termination codons. In order to apply the Cas9-CRISPR method, a Cas9 gene sequence was inserted into a plasmid containing the AUR1-C gene resistant to Aureobasidin A, as an antibiotic, and was expressed in the yeast. Guide DNA and repair DNA targeting the mutated parts of GPD1 and GPD2, respectively, were transformed into the 2,3-butanediol-producing NADH oxidase-expressing strain, to produce strains BD5_T2nox_dGPD1, BD5_T2nox_dGPD2, and BD5_T2_nox_dGPD1dGPD2, in which GPD1 and GPD2 were inactivated.

In addition, pyruvate kinase derived from *Candida tropicalis* was introduced into strain BD5_T2nox_dGPD1dGPD2 expressed by the GPD2 promoter to produce the BD5_T2nox_dGPD1dGPD2_CtPDC1 strain.

Figure 11:
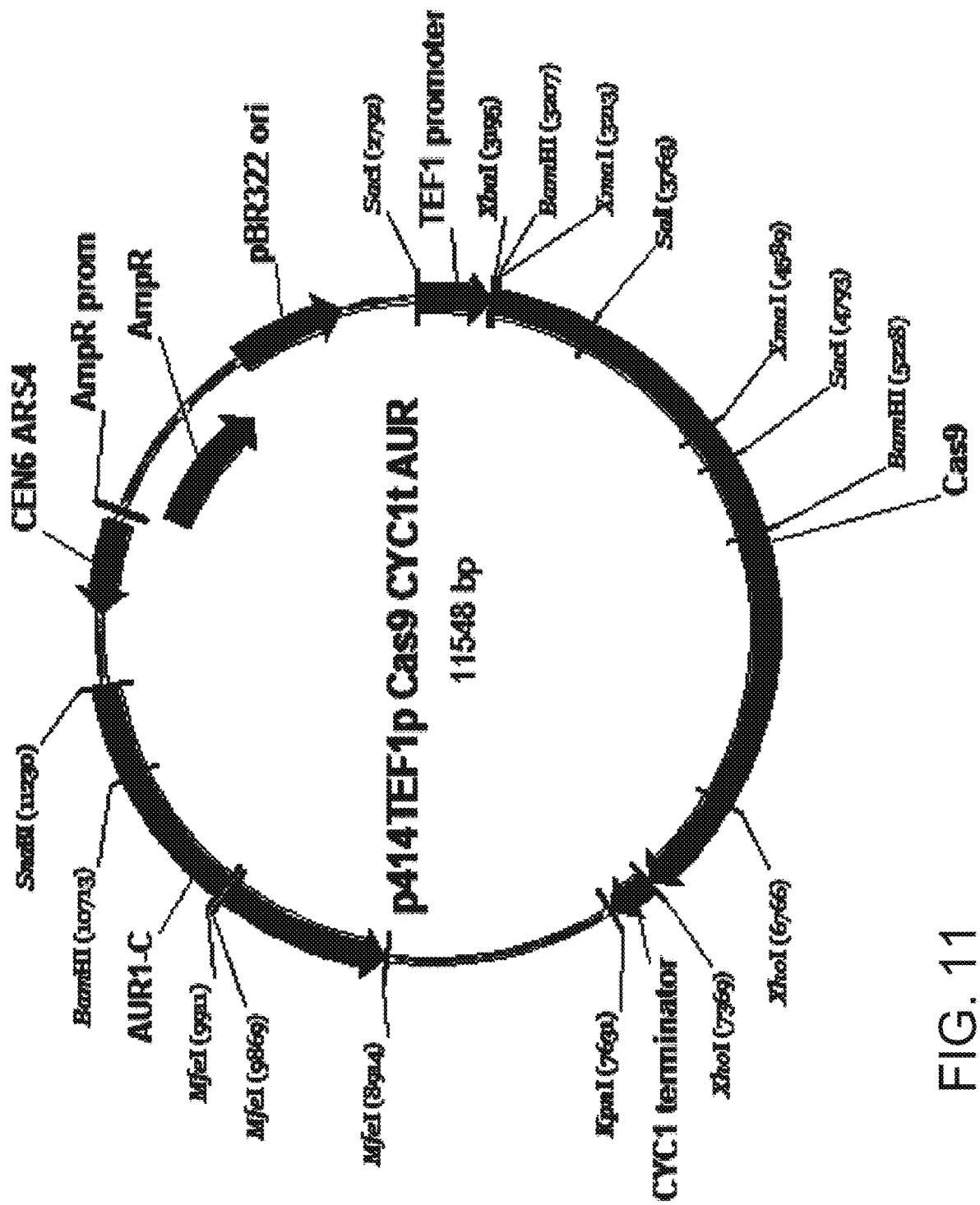
FIG. 11 is a map of a plasmid for Cas9 expression.
Figure 12:
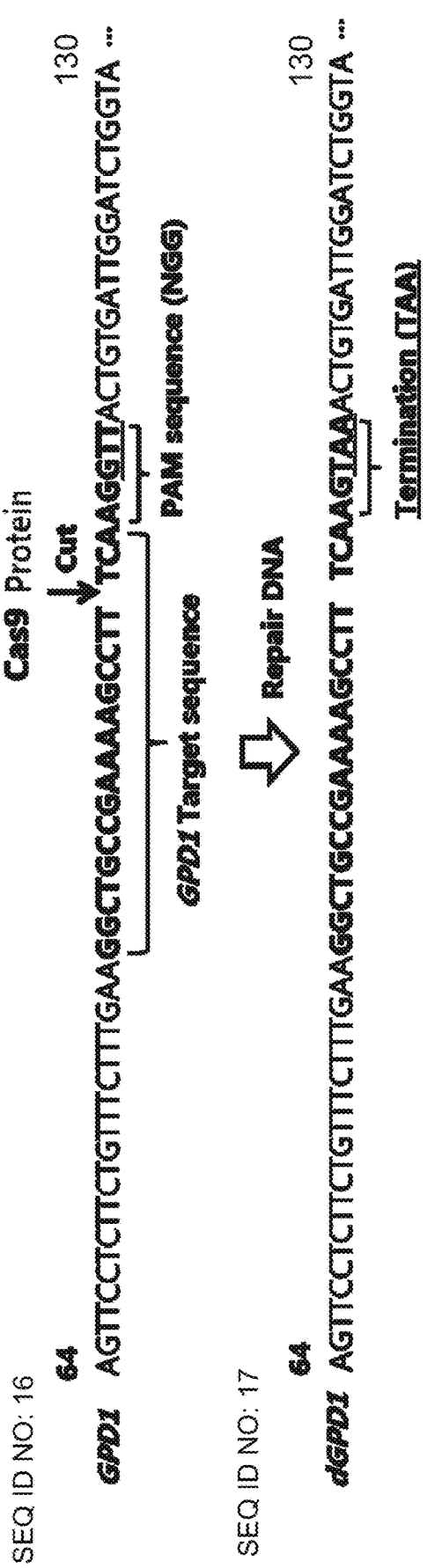
FIG. 12 is a schematic diagram showing a point mutation process for removing GPD1 genes.
Figure 13:
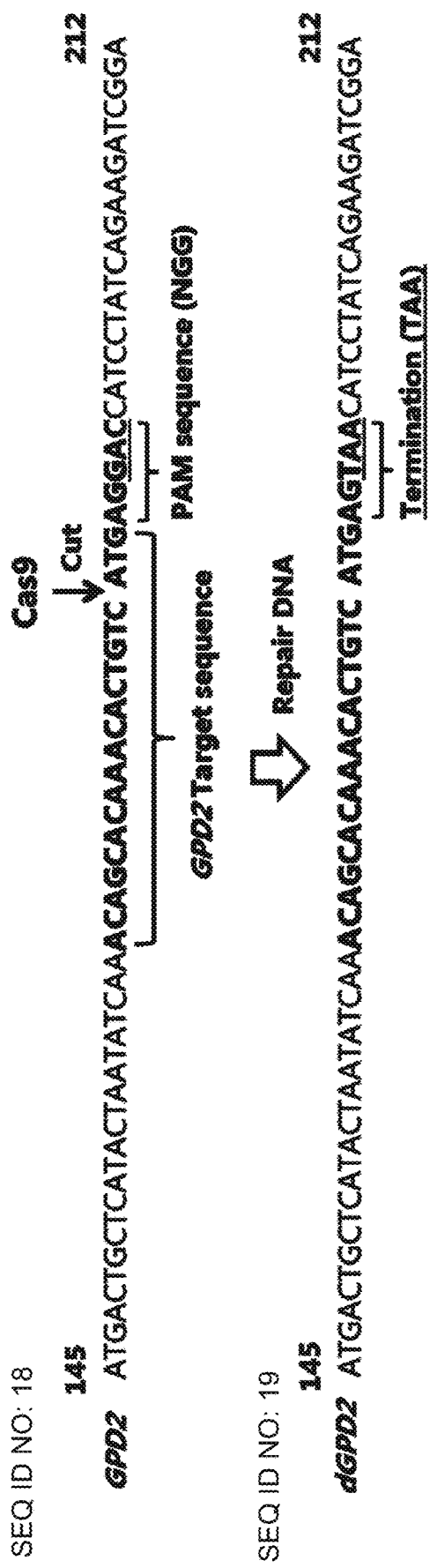
FIG. 13 is a schematic diagram showing a point mutation process for removing GPD2 genes.

FIG. 11 is a map of a plasmid for Cas9 expression. FIG. 12 is a schematic diagram showing a point mutation process for removing GPD1 genes. FIG. 13 is a schematic diagram showing a point mutation process for removing GPD2 genes. FIG. 14 shows a sequence of GPD1 genes, activity of which is removed, wherein the mutated site is underlined. FIG. 15 shows a sequence of GPD2 genes, activity of which is removed, wherein the mutated site is underlined.

Example 13: Production of GPD1 and GPD2-Free Strains with No NADH Oxidase Activity Strains for producing 2,3-butanediol having no NADH oxidase activity were produced by removing the plasmid for expressing NADH oxidase from BD5_T2nox_dGPD1, BD5_T2nox_dGPD2 and BD5_T2nox_dGPD1dGPD2 strains prepared in Example 12.

For this purpose, BD5_T2nox_dGPD1, BD5_T2nox_dGPD2 and BD5_T2nox_dGPD1dGPD2 strains were repeatedly sub-cultured in a medium containing uracil, which is a marker of plasmid for expressing NADH oxidase, and strains, from which the NADH oxidase plasmid was removed, were selected in a medium containing uracil and in a medium containing no uracil by replica plating.

Figure 16:
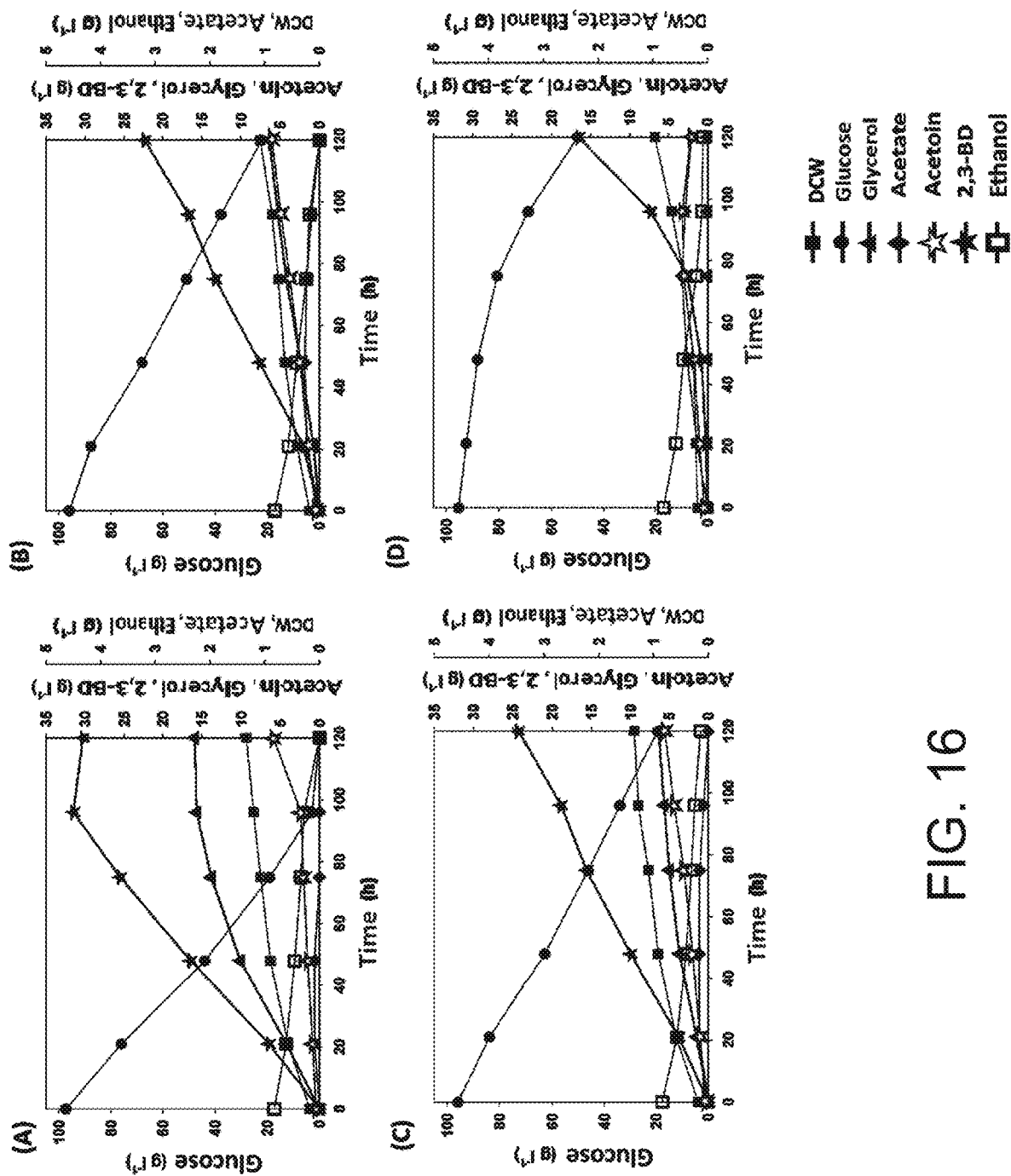
FIG. 16 shows a fermentation profile of GPD gene-removed strains. A: BD5p426TDH3_L1nox, B: BD5_T2nox_dGPD1, C: BD5_T2nox_dGPD2; D: BD5_T2nox_dGPD1dGPD2.

As a result, in case of the BD5_T2nox_dGPD1 strains, NADH oxidase was removed from five strains out of 16 strains in total, and in case of the BD5_T2nox_dGPD2 strains, NADH oxidase was removed from six strains out of 16 strains (Table 6 and FIG. 16).

However, in the case of the strain BD5_T2nox_dGPD1dGPD2, strains, from which NADH oxidase was removed, could be not obtained from 120 strains in total. This means that NADH oxidase is an essential enzyme for growth of Pdc-deficient Gpd-deficient 2,3-butanediol yeast strains. The final conclusion is that NADH oxidase functions to oxidize additional NADH, which is produced by the removal of GPD gene, into NAD$^+$, so that the recombinant strain can grow. FIG. 16 shows results of plasmid curing tests of strains BD5_T2nox_dGPD1, BD5_T2nox_dGPD2 and BD5_T2nox_dGPD1_dGPD2.

TABLE 6

Results of plasmid curing tests of strains BD5_T2nox_dGPD1, BD5_T2nox_dGPD2 and BD5_T2nox_dGPD1_dGPD2.

| Strains | Ura-cell/Total cells | |
|---|---|---|
| BD5_T2nox_dGPD1 | 5/16 | — |
| BD5_T2nox_dGPD2 | 6/16 | — |
| BD5_T2nox_dGPD1_dGPD2 | 0/24 | 0/96 |

Example 14: Fermentation of 2,3-Butanediol Using GPD-Free Strain

Fed-batch culture was carried out using the yeast strain for producing 2,3-butanediol prepared in Example 12. YP medium was used. At the initial stage, 100 g/L of glucose and 0.7 g/L of ethanol were supplied as a carbon source. Cell inoculation concentration, culture temperature, culture conditions and the like were the same as in Example 3.

As a result of the culture, as compared to the glycerol yield (0.166 $g_{Glycerol}$/$g_{Glucose}$) of control group, the strain, from which GPD1 was removed, had a decreased glycerol yield of 0.086 $g_{Glycerol}$/$g_{Glucose}$ and the strain, from which GPD2 was removed, was decreased to 0.083 $g_{Glycerol}$/$g_{Glucose}$. In addition, glycerol was not observed in the strain from which both GPD1 and GPD2 were removed, and the yield of 2,3-butanediol was 0.363 $g_{2,3\text{-}butanediol}$/$g_{Glucose}$, which was increased by 10% as compared with the control group (FIG. 16, Table 7).

FIG. 16 shows fermentation profiles of the GPD gene-free strains. A: BD5_p426TDH3_L1nox, B: BD5_T2nox_dGPD1, C: BD5_T2nox_dGPD2, D: BD5_T2nox_dGPD1dGPD2.

TABLE 7

Fermentation results of GPD gene-free strains

| Parameters | $DCW_{max}$ (g/L) | Glycerol (g/L) | Acetoin (g/L) | 2,3-BD (g/L) | Glycerol yield (g/g) | 2,3-BD yield (g/g) | 2,3-BD productivity (g/L · h$^{-1}$) |
|---|---|---|---|---|---|---|---|
| BD5_T2nox | 1.3 | 15.7 | 1.9 | 31.5 | 0.166 | 0.333 | 0.33 |
| BD5_T2nox_dGPD1 | 1.1 | 6.4 | 5.6 | 22.3 | 0.086 | 0.302 | 0.19 |
| BD5_T2nox_dGPD2 | 1.1 | 6.4 | 5.1 | 24.3 | 0.083 | 0.317 | 0.20 |
| BD5_T2nox_dGPD1_dGPD2 | 1.0 | 0 | 1.7 | 16.5 | 0 | 0.363 | 0.14 |

Example 15: Production of High-Concentration and High-Productivity 2,3-Butanediol by Batch and Fed-Batch Culture and Oxygen Supply Control In order to identify the industrial applicability of the strain for producing 2,3-butanediol prepared in Example 14, high-concentration 2,3-butanediol was produced by batch and fed-batch culture methods. The strain used was BD5_T2nox_dGPD1dGPD2_CtPDC1 and the initial cell inoculation concentration was 3.4 gDCW/L. The fermentation temperature was maintained at 30° C. For batch culture, 300 g/L of glucose was added to YP medium at the initial stage. For fed-batch culture, 100 g/L of glucose was added and 150 g/L of glucose was added at the middle of fermentation. The initial oxygen supply was 2 vvm, 400 rpm, and the oxygen supply was reduced to 1 vvm, 200 rpm and 2 vvm 300 rpm in the middle of fermentation.

Figure 17:
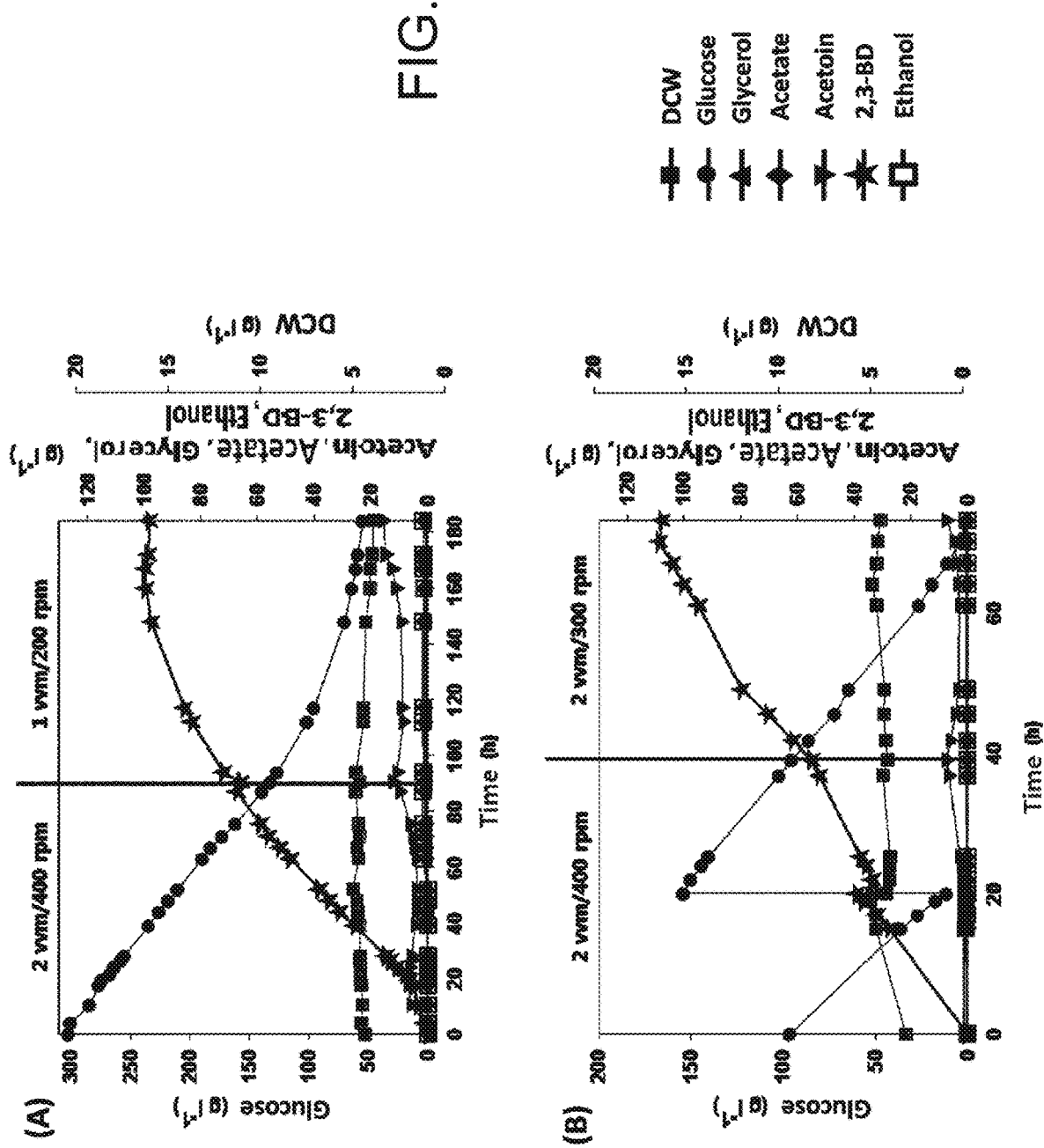
FIG. 17 shows a high-concentration 2,3-butanediol fermentation profile using strain BD5_T2nox_dGPD1dGPD2. A: batch culture, B: fed-batch culture.

The test results are shown in FIG. 17 and Table 8.

As a result of the batch culture, 237.9 g/L of glucose was consumed from 300 g/L of glucose, resulting in production of 99.4 g/L of 2,3-butanediol therefrom. At this time, the yield of 2,3-butanediol was 0.418 $g_{2,3\text{-}butanediol}/g_{Glucose}$, and the productivity thereof was 0.62 $g_{2,3\text{-}Butanediol}/L/h$.

As a result of the fed-batch culture, 108.6 g/L of 2,3-butanediol was produced during culture for 70 hours. At this time, the yield of 2,3-butanediol was 0.495, which corresponded to 99% of the theoretical yield. By-products of glycerol, acetic acid and ethanol were not produced at all, and acetoin was produced at 3.5 g/L. The productivity of 2,3-butanediol could be improved by minimizing the inhibitory effect of Gpd-removed strains by high-concentration glucose through fed-batch culture. In addition, the amount of oxygen fed into the medium could regulate NADH oxidase activity, thereby contributing to the growth of strains and minimizing production of acetoin by-products.

FIG. 17 shows a high-concentration 2,3-butanediol fermentation profile using BD5_T2nox_dGPD1dGPD2 strain. A: batch culture, B: fed-batch culture.

As apparent from the foregoing, methods for producing 2,3-butanediol using conventional yeasts had a limitation in obtaining 2,3-butanediol with low productivity.

However, the yeast strain for producing 2,3-butanediol according to the present invention can synthesize acetyl-CoA, while avoiding production of ethanol by introducing *Candida tropicalis*-derived Pdc, which is less active than its own pyruvate decarboxylase (Pdc), into the strain, thereby increasing the strain growth rate and the substrate consumption rate and ultimately greatly improving productivity of 2,3-butanediol.

That is, conventional Pdc-deficient strains did not produce acetyl-CoA in addition to ethanol biosynthesis due to the deficiency of Pdc, such that the strains could not grow efficiently. The present invention can solve this problem by introducing *Candida* tropicallis-derived Pdc into cells of the strain. Thus, according to the present invention, a high concentration of 2,3-butanediol can be produced with high productivity.

Conventional methods for producing 2,3-butanediol using recombinant *Saccharomyces cerevisiae* (yeast) result in production of a large amount of glycerol as a by-product, in addition to the production of 2,3-butanediol. However, when the recombinant *Saccharomyces cerevisiae* strain according to the present invention is used, 2,3-butanediol can be produced with high purity, high yield and high productivity, while inhibiting production of glycerol.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

TABLE 8

High-concentration 2,3-butanediol fermentation profile using BD5_T2nox_dGPD1dGPD2 strain

| Condition | Glucose consumed (g/L) | Glycerol (g/L) | Acetoin (g/L) | 2,3-BD (g/L) | Acetate (g/L) | Ethanol (g/L) | Glycerol yield (g/g) | 2,3-BD yield (g/g) | 2,3-BD productivity (g/L · h$^{-1}$) |
|---|---|---|---|---|---|---|---|---|---|
| Batch | 237.9 | 0.5 | 11.3 | 99.4 | 1.3 | 0.2 | 0.002 | 0.418 | 0.62 |
| Dumping | 235.1 | 0.2 | 3.5 | 108.6 | 0.1 | 0 | 0.001 | 0.495 | 1.55 |

What is claimed is:

1. A recombinant *Saccharomyces cerevisiae* for producing 2,3-butanediol,
    wherein GPD1 and GPD2 genes encoding glycerol-3-phosphate dehydrogenase are removed and a gene encoding an NADH oxidase is introduced in the recombinant *Saccharomyces cerevisiae*,
    wherein a pyruvate decarboxylase gene is inactivated and a *Candida tropicalis* PDC1 gene encoding *Candida tropicalis* pyruvate decarboxylase 1 is introduced in the recombinant *Saccharomyces cerevisiae*, wherein the *Candida tropicalis* PDC1 gene is operably linked to a GPD2 promoter, and
    wherein the recombinant *Saccharomyces cerevisiae* is transformed so as to express acetolactate synthase, is transformed so as to express acetolactate decarboxylase, and is transformed so as to express butanediol dehydrogenase.

2. The recombinant *Saccharomyces cerevisiae* according to claim 1, wherein the transformation so as to express the acetolactate synthase is carried out by introducing an alsS gene encoding alpha-acetolactate synthase,
    the transformation so as to express acetolactate decarboxylase is carried out by introducing an alsD gene encoding alpha-acetolactate decarboxylase, and
    the transformation so as to express butanediol dehydrogenase is carried out by overexpressing a *Saccharomyces cerevisiae* BDH1 gene encoding *Saccharomyces cerevisiae* 2,3-butanediol dehydrogenase.

3. The recombinant *Saccharomyces cerevisiae* according to claim 1, wherein the inactivation of a pyruvate decarboxylase gene is carried out by partially disrupting or knocking out one or more genes selected from PDC1, PDC5 and PDC6.

4. The recombinant *Saccharomyces cerevisiae* according to claim 1, wherein the NADH oxidase is a *Lactobacillus lactis* NADH oxidase.

5. The recombinant *Saccharomyces cerevisiae* according to claim 1, wherein the gene encoding an NADH oxidase is inserted into a p426GPD plasmid, which is a multi-copy plasmid, and wherein the gene encoding an NADH oxidase is operably linked to a TDH3 promoter.

6. A method for producing 2,3-butanediol comprising culturing the recombinant *Saccharomyces cerevisiae* of claim 1 in a medium supplemented with glucose to thereby produce 2,3-butanediol.

7. The method according to claim 6, wherein the method is carried out while continuously supplying oxygen.

8. The method according to claim 7, wherein the continuous supply of oxygen is carried out by continuously feeding oxygen such that an amount of oxygen supplied in the middle stage of fermentation is lower than an amount of oxygen supplied in an initial stage of fermentation.

9. The method according to claim 6, wherein the culture is fed-batch culture comprising continuously supplying glucose.

* * * * *